United States Patent
Tingay et al.

(10) Patent No.: US 10,393,675 B2
(45) Date of Patent: *Aug. 27, 2019

(54) X-RAY INSPECTION APPARATUS

(71) Applicant: NORDSON CORPORATION, Westlake, OH (US)

(72) Inventors: John Tingay, Cambridge (GB); William T. Walker, Suffolk (GB); Phil King, Essex (GB); Simon White, Suffolk (GB); Kate Donaldson-Stewart, Essex (GB)

(73) Assignee: Nordson Corporation, Westlake, OH (US)

( * ) Notice: Subject to any disclaimer, the term of this patent is extended or adjusted under 35 U.S.C. 154(b) by 281 days.

This patent is subject to a terminal disclaimer.

(21) Appl. No.: 15/300,775

(22) PCT Filed: Apr. 3, 2015

(86) PCT No.: PCT/US2015/024245
§ 371 (c)(1),
(2) Date: Sep. 29, 2016

(87) PCT Pub. No.: WO2015/153970
PCT Pub. Date: Oct. 8, 2015

(65) Prior Publication Data
US 2017/0025317 A1   Jan. 26, 2017

(30) Foreign Application Priority Data

Apr. 4, 2014   (EP) .................................... 14163620
Aug. 8, 2014   (EP) .................................... 14180382

(51) Int. Cl.
G01N 23/04   (2018.01)
H01L 21/67   (2006.01)
(Continued)

(52) U.S. Cl.
CPC ....... *G01N 23/04* (2013.01); *H01L 21/67288* (2013.01); *H01L 21/681* (2013.01);
(Continued)

(58) Field of Classification Search
CPC ............. G01N 23/04; G01N 2223/309; G01N 2223/6113; G01N 2223/6116;
(Continued)

(56) References Cited

U.S. PATENT DOCUMENTS 6,028,910 A   2/2000 Kirchner et al.
6,301,330 B1  10/2001 Kurtz et al.
(Continued)

FOREIGN PATENT DOCUMENTS

CN   1766930 A   5/2006
CN   101776618 A  7/2010
(Continued)

OTHER PUBLICATIONS

International Application No. PCT/US2015/024245: International Preliminary Report on Patentability dated Oct. 4, 2016, 12 pages.
(Continued)

*Primary Examiner* — Courtney D Thomas
(74) *Attorney, Agent, or Firm* — Baker & Hostetler LLP

(57) ABSTRACT

An x-ray inspection system including a cabinet containing an x-ray source, a sample support for supporting a sample to be inspected, and an x-ray detector; an air mover configured to force air into the cabinet through an air inlet above the sample support, where the air mover and cabinet are configured to force air through the cabinet from the air inlet past the sample support to an air outlet in the cabinet below the sample support, and an assembly for positioning the sample support relative to the x-ray source and x-ray detector. The sample support includes an upper surface extending in a horizontal plane and the sample positioning assembly
(Continued)

includes a vertical positioning mechanism for moving the sample support in a vertical direction, orthogonal to the horizontal plane, and a first horizontal positioning mechanism for moving the sample support and vertical positioning mechanism in a first horizontal direction.

24 Claims, 15 Drawing Sheets

(51) Int. Cl.
H01L 21/66 (2006.01)
H01L 21/68 (2006.01)
H01L 21/683 (2006.01)

(52) U.S. Cl.
CPC .......... *H01L 21/6838* (2013.01); *H01L 22/12* (2013.01); *G01N 2223/309* (2013.01); *G01N 2223/6113* (2013.01); *G01N 2223/6116* (2013.01); *G01N 2223/6462* (2013.01)

(58) Field of Classification Search
CPC ...... G01N 2223/6462; H01L 21/67288; H01L 21/681; H01L 21/6838; H01L 22/12
USPC ..................................... 378/58, 62
See application file for complete search history.

(56) References Cited

U.S. PATENT DOCUMENTS

| | | | |
|---|---|---|---|
| 6,331,890 B1 | 12/2001 | Marumo et al. | |
| 6,434,217 B1 | 8/2002 | Pickelsimer et al. | |
| 6,672,761 B2 | 1/2004 | Sykes et al. | |
| 6,686,991 B1* | 2/2004 | Binnard | G03F 7/70716 |
| | | | 250/492.2 |
| 6,834,117 B1 | 12/2004 | Rao et al. | |
| 6,834,447 B1 | 12/2004 | Currey | |
| 7,099,432 B2* | 8/2006 | Ichihara | G01N 23/046 |
| | | | 378/25 |
| 7,241,993 B2 | 7/2007 | Nakasuji et al. | |
| 7,369,695 B2 | 5/2008 | Zettel et al. | |
| 7,406,152 B2 | 7/2008 | Teramoto et al. | |
| 8,120,304 B2 | 2/2012 | Yalei et al. | |
| 8,400,789 B2 | 3/2013 | Joshi | |
| 8,408,789 B2 | 4/2013 | Takahara | |
| 8,509,512 B2 | 8/2013 | Ota et al. | |
| 8,596,866 B2 | 12/2013 | Matoba | |
| 8,848,868 B2 | 9/2014 | Davydov et al. | |
| 9,129,427 B2 | 9/2015 | Golubovic et al. | |
| 10,215,716 B2* | 2/2019 | Tingay | G01N 23/04 |
| 2002/0090057 A1 | 7/2002 | Sykes et al. | |
| 2003/0043963 A1 | 3/2003 | Yamagami et al. | |
| 2007/0042313 A1* | 2/2007 | Shibamura | F27B 9/20 |
| | | | 432/121 |
| 2007/0186699 A1* | 8/2007 | Hiltawski | G01N 21/9501 |
| | | | 73/865.8 |
| 2007/0189460 A1 | 8/2007 | Buck et al. | |
| 2008/0043908 A1* | 2/2008 | Teramoto | G01N 23/046 |
| | | | 378/57 |
| 2010/0148715 A1 | 6/2010 | Yalei et al. | |
| 2010/0172561 A1 | 7/2010 | Ota et al. | |
| 2011/0051894 A1* | 3/2011 | Takahara | G01N 23/223 |
| | | | 378/86 |
| 2012/0027174 A1* | 2/2012 | Takamura | A61B 6/00 |
| | | | 378/62 |
| 2012/0032079 A1* | 2/2012 | Nakasuji | G01N 23/225 |
| | | | 250/310 |
| 2012/0140883 A1 | 6/2012 | Iwakiri et al. | |
| 2012/0144938 A1 | 6/2012 | Inagaki et al. | |
| 2013/0108017 A1 | 5/2013 | Golubovic et al. | |
| 2017/0018467 A1* | 1/2017 | Walker | G01N 23/04 |

FOREIGN PATENT DOCUMENTS

| | | |
|---|---|---|
| CN | 102004113 A | 4/2011 |
| CN | 102213683 A | 10/2011 |
| CN | 102525507 A | 7/2012 |
| CN | 103106682 A | 5/2013 |
| DE | 60137996 U | 5/2002 |
| DE | 102011005732 A1 | 9/2012 |
| EP | 1191827 A2 | 3/2002 |
| EP | 1662252 A1 | 5/2006 |
| EP | 2063261 A1 | 5/2009 |
| EP | 2587515 A1 | 5/2013 |
| JP | 2001-135691 A | 5/2001 |
| JP | 2001-153819 A | 6/2001 |
| JP | 2001-318062 A | 11/2001 |
| JP | 2002-181738 A | 6/2002 |
| JP | 2004-170226 A | 6/2004 |
| JP | 2008-245999 A | 10/2008 |
| JP | 2011-075351 A | 4/2011 |
| TW | 200603196 A | 1/2006 |
| TW | 201100986 A | 1/2011 |
| TW | 201329439 A | 7/2013 |
| WO | 2011/039945 A1 | 4/2011 |
| WO | 2012/123216 A1 | 9/2012 |

OTHER PUBLICATIONS

English Translation of JP Office Action dated Nov. 15, 2018 for JP Application No. 2017503789.
English Translation of CN Office Action dated Jul. 30, 2018 for CN Application No. 201580018573.
English Translation of CN Office Action dated Apr. 19, 2019 for CN Application No. 201580018573.

* cited by examiner

X-RAY INSPECTION APPARATUS

CROSS-REFERENCE TO RELATED APPLICATIONS

This application is a National Stage Application of International patent application no. PCT/US2015/024245, filed Apr. 3, 2015, which claims priority to European patent application Nos. EP 14163620.9, filed Apr. 4, 2014, and EP 14180382.5, filed Aug. 8, 2014, the disclosures of which are incorporated by reference in their entirety

FIELD OF THE INVENTION

The invention relates to x-ray inspection apparatus and in particular to an apparatus and method suitable for inspecting a semiconductor wafer during the processing of the semiconductor wafer to produce integrated circuits. However, aspects of the invention relate to x-ray inspection systems in general and can be applied to systems for inspecting any type of sample.

BACKGROUND TO THE INVENTION

Fabricating integrated circuits is a multiple-step sequence of photolithographic and chemical processing steps during which electronic circuits are gradually created on a wafer made of pure semiconductor, typically silicon. The entire manufacturing process, from start to finish, takes six to eight weeks and is performed in highly specialized facilities referred to as fabrication plants. Fabrication plants require many expensive devices to function. Estimates put the cost of building a new fabrication plant over one billion U.S. dollars, with values as high as $3-4 billion not being uncommon. As a result, processing time in a fabrication plant is very valuable. Any time that a fabrication plant is not operating, for example for maintenance of a machine within the plant, is very undesirable.

So there is a need for all wafer processing steps to be extremely reliable with minimal maintenance required, and also for all processing steps to be made a quick as possible and to take a little space as possible.

As part of making processes reliable and in order to ensure that the circuits being produced operate properly, it is desirable to be able to test wafers for defects and faults at various stages of production. While optical inspection of surface features can be achieved rapidly and reliably, inspection of internal faults, such as voids, cracks and misalignments in deposited conductive elements (such as through silicon vies, copper pillars and bumps) is more difficult. Current methods for detecting these faults require taking a wafer out of the fabrication plant and testing using a focussed ion beam, scanning electron microscope or x-rays. However, as soon as a wafer is taken out of the clean environment of the fabrication plant it is effectively destroyed and can no longer be used.

It would be desirable to be able to accurately test semiconductor wafers for voids, cracks and misalignments in deposited conductive elements, in a more efficient and non-destructive manner. It would also be desirable to be able to test semiconductor wafers for voids, cracks and misalignments in deposited conductive elements quickly, in a manner that does not lead to significantly increased processing time for semiconductor wafers.

SUMMARY OF THE INVENTION

In a first aspect there is provided an x-ray inspection system comprising:

- a cabinet, the cabinet containing an x-ray source, a sample support for supporting a sample to be inspected, and an x-ray detector; and
- an air mover configured to force air into the cabinet through an air inlet in the cabinet above the sample support,
- wherein the air mover and cabinet are configured to force air through the cabinet from the air inlet past the sample support to an air outlet in the cabinet below the sample support.

The cabinet may be constructed to provide an x-ray shield, and may be lead lined for this purpose. It is desirable from a safety perspective to minimise the escape of x-rays from the system.

An x-ray system of this type can be used in a clean room environment to inspect items such as semiconductor wafers. By maintaining a flow of air from above the sample support, past the sample support to an outlet below the sample support, the sample can be protected from any dust and debris. The system is configured such that the flow of air is maintained throughout the operation of the system, i.e. while samples are loaded, imaged, moved and unloaded from the system. The system is configured to provide at least a Class 4 ISO 14644-1 cleanroom environment.

The x-ray source is preferably a sealed x-ray tube. Sealed x-ray tubes require much less maintenance than open x-ray tubes and so are better suited to use in a semiconductor fabrication plant where any time that operation of the plant is stopped for maintenance is very expensive.

The x-ray source preferably comprises a transmission target. The use of a transmission target allows for a very small spot size x-ray source and allows for high magnification within a compact system because the sample being imaged can be brought close to the target. A sealed, transmission target, x-ray tube is particularly advantageous for semiconductor wafer inspection, as this type of x-ray tube can provide high resolution images, good reliability and long maintenance cycles.

The system is preferably configured to perform transmission microscopy. The x-ray detector may be configured to measure attenuation of a primary incident x-ray beam from the x-ray source, to provide a two dimensional image of the sample or a region of the sample.

The system may further comprise a high performance air filter, such as a high-efficiency particulate absorption (HEPA) filter or ultra-low penetration air (ULPA) filter, the air filter being located above the sample support. An air filter of this type ensures that the air flow entering the cabinet through the inlet is free from dust.

In a preferred embodiment, the air mover is positioned above the sample support, and within the cabinet. In this embodiment, the air filter is positioned between the air mover and the sample support. Providing the air mover within the cabinet allows for the production of a compact system. However, it is possible to place the air mover outside of the cabinet.

The system may comprise a plurality of air movers and a plurality of air filters. Ideally the system is configured so that air flow within the cabinet is uniform and laminar and in a downward direction, without any recirculation of air. The number of air movers used can be chosen to suit the geometry of the system components within the cabinet to achieve laminar flow. In a preferred embodiment, the system comprises two air movers and two associated air filters.

The air mover may be a fan. The air filter may be coupled to the air mover. The air mover and air filter may be provided as a fan filter unit. The fan filter unit may comprise an enclosure having an air inlet, a fan within the enclosure and configured to draw air in through the air inlet, an air outlet and a filter plate spanning the air outlet so that air exiting through the air outlet is forced through the filter plate. The fan filter unit may be configured to provide a higher pressure within the enclosure than external to the enclosure. Providing a higher pressure within the fan filter unit improves the uniformity of the air flow through the air filter, which is desirable to prevent any air recirculation within the cabinet.

The fan filter unit may comprise a baffle plate coupled to the fan. The baffle plate is advantageously configured to provide for a uniform air flow through the filter plate. The fan may be located at a centre of the enclosure and the baffle plate may be configured to direct air from the fan to the extremities of the enclosure. The enclosure may have external walls, and the baffle plate may be configured to direct air from the fan towards the external walls.

The air mover may comprise an x-ray shield, such as a lead sheet, arranged to prevent the escape of x-rays from the cabinet through the air mover. The baffle plate within the fan filter unit may be an x-ray shield. It is desirable from a safety perspective to minimise the escape of x-rays from the system.

The x-ray source is advantageously located above the sample support and is fixed relative to the cabinet. Placing the x-ray source above the support allows a sample on the top of the support, and in particular a top surface of the sample, to be brought close to the x-ray source. This is advantageous for providing high magnification images in a compact system. If the x-ray source is located above the sample it is also advantageous for it to be stationary during operation to prevent the generation of any dust or debris from any movement mechanism that might damage the sample. It is also advantageous to keep the x-ray source stationary as it is a relatively bulky and massive component. It also typically requires very large power cables which are relatively inflexible and difficult to move.

The x-ray inspection system may comprise a controller including an image processor. The image processor may be connected to the x-ray detector to receive data from the x-ray detector.

The x-ray inspection system may comprise a first positioning assembly that allows for relative movement between the sample support and the x-ray source, wherein the positioning mechanism is located below the sample support. The first positioning assembly may comprise a first horizontal sample positioning mechanism for moving the sample support in a first horizontal direction, a second horizontal sample positioning mechanism for moving the sample support in a second horizontal direction, and a vertical sample positioning mechanism for moving the sample support in a vertical direction.

In a preferred embodiment, the first positioning assembly is configured so that the first horizontal positioning mechanism moves the sample support and the vertical positioning mechanism in a first horizontal direction. The vertical positioning mechanism may be configured to move both the second horizontal positioning mechanism and the sample support in the vertical direction. The first horizontal positioning mechanism is preferably mounted directly to a supporting frame. This arrangement is advantageous for a system that performs a raster scan of the sample in the horizontal plane. The scan lines of the raster scan extend in the second horizontal direction so the second horizontal positioning mechanism is required to operate over the longest distance, frequently and fast.

Accordingly the second horizontal positioning mechanism is configured to move only the sample support and not the mass of any of the other positioning mechanisms. The first horizontal positioning mechanism is also required to move fast and frequently compared with the vertical positioning mechanism. By mounting the first horizontal positioning mechanism directly to a supporting frame, movement in the first horizontal direction can be made fast and accurate. The vertical positioning mechanism alters the image magnification and is required to move relatively infrequently, over a relatively shorter distance that the horizontal positioning mechanisms, and typically not at all during a raster scanning operation. The vertical positioning assembly can be made relatively less massive than the horizontal positioning mechanisms.

The supporting frame, to which the first horizontal positioning mechanism is fixed, may be mounted to the floor. In a preferred embodiment, the supporting frame comprises a first rigid sub-frame configured to be fixed to the floor, and a second rigid sub-frame supported on the first sub-frame through a damping mechanism, with the first horizontal positioning mechanism fixed to the second rigid sub-frame.

The x-ray inspection system may comprise a sample support position detection assembly comprising non-contact position measuring device, such as a laser interferometer, positioned adjacent to the sample support and configured to detect a position or change in position of the sample support. This is particularly advantageous for determining precisely the position of the sample within the horizontal plane, which is required when producing very high magnification images and using them to produce a three dimensional model. In a preferred embodiment, the system comprises two non-contact position measuring devices, preferably laser interferometers. A first non-contact position measuring device for detecting changes in position of the sample support in the first horizontal direction and a second non-contact position measuring device for detecting changes in position of the sample support in the second horizontal direction. Of course, a pair of non-contact position measuring devices could be arranged to detect changes in position in different directions within a horizontal plane than the first and second horizontal directions. Other possible non-contact position measuring devices include optical linear encoders, magnetic encoders, capacitive sensors and sonar distance measuring devices.

The position information provided by the non-contact position measuring device or devices may be used by the image processor. In particular, the change of position of the sample from image to image provided by the non-contact position measuring device or devices can be used in a tomosynthesis calculation. Precise positional information is required when producing a three dimensional model of very small features such as voids in a semiconductor wafer, at very high magnification. The more precise the positional information for the sample, the better the image resolution.

The x-ray inspection system may comprise a proximity sensor fixed to the x-ray source configured to provide a measurement of distance between the x-ray source and a surface of a sample on the sample support. The proximity sensor may be a laser position sensor or a confocal sensor. The proximity sensor may be connected to the image processor to provide distance data to the image processor. The image processor may use the measurement of distance from the proximity sensor in an image processing calculation, such as a tomosynthesis calculation.

The controller may be connected to the sample positioning assembly and may control the sample positioning assembly based on the measurement of distance provided by the proximity sensor. The proximity sensor provides an accurate distance measurement between the x-ray source and a top surface of a sample, which can be used both in an image processing calculation, such as a magnification calculation, and to prevent any collision of the sample and the x-ray source. To provide a useful inspection of small features in a semiconductor wafer in a compact system, the sample is brought very close to the x-ray source, but any collision between the sample and the x-ray source would likely damage both the sample and the x-ray source. Avoiding such collisions, while bringing the sample very close to the x-ray source, is therefore necessary.

The sample positioning assembly may comprise a linear encoder. The controller may be configured to calibrate the linear encoder based on the measurement of distance provided by the proximity sensor.

The x-ray inspection system may further comprise a second positioning assembly that allows for relative movement between the x-ray detector and the x-ray source, wherein the second positioning mechanism is located below sample support. The second positioning assembly may comprise a horizontal detector positioning mechanism for moving the detector in at least two non-parallel directions within a horizontal plane. The detector positioning mechanism may comprise a detector tilting mechanism configured to allow the detector to be tilted from the horizontal plane about at least two non-parallel axes. The detector can then be tilted so that an imaging surface of the detector is always normal to a line between a centre of the detector and the output spot of the x-ray source, wherever the detector is positioned. The controller may be connected to the second positioning assembly.

The first and second positioning assemblies are advantageously positioned below the sample support. The ability to move the sample and detector relative to the x-ray source allows for different portions of the sample to be imaged and different angles of inspection to be used. A series of images of the same sample, or the same portion of a sample, can be used in a tomosynthesis system to generate three dimensional models and images of the sample and accurately locate and measure cracks, voids and other defects.

By locating a fixed x-ray source above the sample, and the positioning assemblies beneath the sample, all the moving components of the system can be located underneath the sample. With a downwardly directed airflow, this reduces the likelihood of any debris generated by the moving parts reaching and damaging the sample.

The system may comprise a perforated deck positioned below the x-ray source but above the first and second positioning assemblies. The perforated deck and air mover are configured to provide a first air pressure above the deck and a second air pressure below the deck, wherein the second air pressure is lower than the first air pressure. The perforated deck is preferably positioned level with the height of the sample support when the sample support is in its uppermost position (which corresponds to maximum magnification). Even a small pressure difference between the space above the sample and the space below the sample prevents any significant flow of air from below the sample to above the sample.

The air inlet advantageously comprises a labyrinthine air flow path. This ensures that x-rays from the x-ray source cannot escape from the cabinet through the air inlet. The air outlet advantageously comprises a labyrinthine air flow path for the same reason. The air outlet is preferably large to minimise any recirculation of air.

The sample support is configured to support the sample during x-ray inspection. In one embodiment, the sample support is configured to support a semiconductor wafer.

The sample support may be configured in accordance with one of the eleventh to fifteenth aspects of the invention, described below.

The ability to inspect semiconductor wafers for internal features in a non-destructive fashion during wafer processing is highly desirable. By providing a system in which air flow is directed through the cabinet from above the wafer to below the wafer, while the cabinet still provides the required x-ray shielding, this becomes possible.

The use of air filters, such as those found in fan filter units, a perforated deck level with the sample support, and the positioning of the x-ray source in a fixed position above the sample support, ensure that clean room standards can be met. Further advantageous features, such as the use of a sealed transmission target x-ray tube, provide the required reliability and image quality for a commercially attractive system.

In a second aspect of the invention, there is provided a method of inspecting a semiconductor wafer comprising:
  directing x-rays at the wafer;
  detecting x-rays that have passed through the wafer; and
  directing a laminar airflow from above the wafer, past the wafer to below the wafer simultaneously with the steps of directing and detecting.

The air flow preferably comprises HEPA or ULPA filtered air.

By providing a continuous flow of clean air past the wafer, with no recirculation of air that might have picked up dust or debris from mechanisms within the system, the inspection system can meet clean room standards and the risk of contamination of or damage to the semiconductor wafer is minimised.

In a third aspect of the invention, there is provided an x-ray inspection system comprising: an x-ray source, a sample support configured to support a semiconductor wafer to be inspected, and an x-ray detector; wherein the x-ray source is positioned above the sample support.

The x-ray source is preferably fixed to a supporting frame and does not move during operation of the system. The sample support may be positioned very close to the x-ray source to allow for the production of high magnification images.

In this aspect, the x-ray inspection system may comprise a cabinet, the cabinet containing the x-ray source, the sample support and the x-ray detector; and an air mover configured to force air into the cabinet through an air inlet in the cabinet above the sample support, wherein the air mover and cabinet are configured to force air through the cabinet from the air inlet past the sample holder to an air outlet in the cabinet below the sample holder.

The sample support may comprise a support surface extending in a horizontal plane and further comprise a sample support positioning assembly for positioning the sample support relative to the x-ray source or x-ray detector, the support positioning assembly being positioned below the sample support.

The first sample positioning assembly may comprise a vertical positioning mechanism for moving the sample support in a vertical direction, orthogonal to the horizontal plane, and a first horizontal positioning mechanism for moving the sample support and the vertical positioning mechanism in a first horizontal direction. The x-ray inspection system may further comprise a second positioning assembly that allows for movement between the x-ray detector and the x-ray source, wherein the second positioning mechanism is located below the sample support.

In a fourth aspect of the invention, there is provided an x-ray inspection system comprising: an x-ray source, a sample support for supporting a sample to be inspected, wherein the sample support comprises a support surface extending in a horizontal plane, an x-ray detector; and a sample support positioning assembly for positioning the sample support relative to the x-ray source or x-ray detector; wherein the sample positioning assembly comprises a vertical positioning mechanism for moving the sample support in a vertical direction, orthogonal to the horizontal plane, and a first horizontal positioning mechanism for moving the sample support and the vertical positioning mechanism in a first horizontal direction.

The sample positioning assembly may comprise a second horizontal positioning mechanism configured to move the sample support in a second horizontal direction, non-parallel to the first horizontal direction, wherein the vertical positioning mechanism is configured to move both the second horizontal positioning mechanism and the sample support in the vertical direction.

The system may further comprise a controller connected to the first and second horizontal positioning mechanisms and configured to control the horizontal positioning mechanisms to move the sample support to perform a raster scan in horizontal plane relative to the x-ray source. Advantageously the scan lines extend in the second horizontal direction. The second horizontal positioning mechanism is required to operate over the longest distance, frequently and fast. Accordingly the second horizontal positioning mechanism is configured to move only the sample support and not the mass of any of the other positioning mechanisms. The first horizontal positioning mechanism is also required to move fast and frequently compared with the vertical positioning mechanism. By mounting the first horizontal positioning mechanism directly to a rigid supporting frame, movement in the first horizontal direction can be made fast and accurate.

The system may be configured such that the vertical positioning mechanism has a shorter range of travel than the first and second horizontal positioning mechanisms. The system may be configured such that the vertical positioning mechanism operates to move the sample support more slowly than the first and second horizontal positioning mechanisms.

The vertical positioning mechanism alters the image magnification and is typically required to move relatively infrequently, over a relatively shorter distance that the horizontal positioning mechanisms, and typically not at all during a raster scanning operation. Because the vertical positioning assembly does not need to move as far or as fast as the horizontal positioning mechanisms, the vertical positioning assembly can be made relatively less massive than the horizontal positioning mechanisms.

The positioning assembly may comprise a plurality of motors. In particular, the first and second horizontal positioning mechanisms may each comprise one or more linear motors. The vertical positioning assembly may comprise a servo motor together with a lead screw. The system may advantageously be configured to control the mechanisms within the positioning assembly to move the sample support to a plurality of predetermined imaging positions.

The x-ray inspection system advantageously further comprises a frame configured to be fixed to a floor, wherein the first horizontal positioning mechanism is fixed to the frame. By fixing the first horizontal positioning assembly directly to a supporting frame, the first horizontal positioning assembly can be made fast and accurate. The frame may be formed in two or more parts connected to one another through damping components to reduce vibration of the sample support.

The sample support may be configured to support a semiconductor wafer. The sample support may be configured in accordance with one of the eleventh to fifteenth aspects of the invention.

The x-ray source is preferably located above the sample support. The x-ray source is preferably a sealed x-ray tube, with a transmission target, as described in relation to the first aspect of the invention.

The x-ray inspection system may further comprise a sample support position detection assembly comprising a non-contact position measuring device, such as a laser interferometer, positioned adjacent to the sample support and configured to detect a position or change of position of the sample support, as described in more detail with reference to the fifth aspect of the invention.

The x-ray inspection system may further comprise a proximity sensor fixed to the x-ray source for determining a distance between the x-ray source and a surface of a sample on the sample support, as described in more detail with reference to the sixth, seventh and eighth aspects of the invention.

The system may be configured to perform a tomosynthesis calculation based on images recorded by the x-ray detector.

The x-ray inspection system may comprise a detector positioning assembly for positioning the x-ray detector relative to the x-ray source, wherein the detector positioning assembly comprises a horizontal detector positioning mechanism for moving the detector in at least two non-parallel directions within a horizontal plane, and a detector tilting mechanism configured to allow the detector to be tilted from the horizontal plane about at least two non-parallel axes. Advantageous features of the detector positioning assembly are described in more detail with reference to the ninth and tenth aspects of the invention.

In a fifth aspect of the invention, there is provided an x-ray inspection system comprising: an x-ray source, a sample support for supporting a sample to be inspected, an x-ray detector; a sample positioning assembly for positioning the sample support relative to the x-ray source or x-ray detector; a sample support position detection assembly comprising a non-contact position measuring device positioned adjacent to the sample support and configured to detect a position or change of position of the sample support; and an image processor connected to the sample support position detection assembly.

The non-contact position measuring device may be a laser interferometer. The x-ray inspection system may further comprise a reflector mounted to the sample support to reflect laser light from the interferometer.

The system may be configured to automatically move the sample positioning assembly to a plurality of imaging positions, wherein the image processor is configured to calculate a change in a position of the sample support from one imaging position to another based on an output from the non-contact position measuring device. The image processor may be configured to perform a tomosynthesis calculation on images recorded by the x-ray detector, using the output from the non-contact position measuring device.

The sample support may comprise a support surface extending in a horizontal plane. The sample positioning assembly may comprise a first positioning mechanism for moving the sample support in a first horizontal direction and a second positioning mechanism for moving the sample support in a second horizontal direction. The sample support position detection assembly may then comprise a first non-contact position measuring device for detecting a position or a change of position of the sample support in the first horizontal direction and a second non-contact position measuring device for detecting a position or a change of position of the sample support in the second horizontal direction. The second non-contact position measuring device is preferably a second laser interferometer and the x-ray inspection system may further comprise a second reflector mounted to the sample support to reflect laser light from the second interferometer.

In a system with two or more interferometers there may be two or more corresponding laser light sources. Alternatively, the system may comprise one or more beam splitters configured to split a laser light beam into two secondary beams which can then be used with different interferometers.

The sample positioning assembly may comprise a vertical positioning mechanism for moving the sample support in a vertical direction, orthogonal to the horizontal plane and wherein the sample support position detection assembly may comprise a third non-contact position measuring device for detecting position or movement of the sample support in the vertical direction. The third non-contact position measuring device may be positioned to detect a vertical position of the sample support or may be positioned to detect a vertical position of a top surface of a sample mounted on the sample support. The controller may be configured to perform a magnification calculation based on an output of the third non-contact position measuring device.

The non-contact position measuring device or each non-contact position measuring device may be a homodyne interferometer or a heterodyne interferometer. Other possible non-contact position measuring devices include optical linear encoders, magnetic encoders, capacitive sensors and sonar distance measuring devices.

The x-ray source is advantageously located above the sample support. The sample support may be configured to support a semiconductor wafer. The sample support may be configured in accordance with one of the eleventh to fifteenth aspects of the invention.

The x-ray inspection system may comprise a proximity sensor fixed to the x-ray source and configured to determine a distance between the x-ray source and a surface of a sample on the sample support. An output of the proximity sensor may be connected to the controller. The proximity sensor may be as described in more detail in relation to the sixth, seventh and eighth aspects of the invention.

The x-ray inspection system may comprise a detector positioning assembly for positioning the x-ray detector relative to the x-ray source, wherein the detector positioning assembly comprises a horizontal detector positioning mechanism for moving the detector in at least two non-parallel directions within a horizontal plane, and a detector tilting mechanism configured to allow the detector to be tilted from the horizontal plane about at least two non-parallel axes. Advantageous features of the detector positioning assembly are described in more detail with reference to the ninth and tenth aspects of the invention.

In a sixth aspect of the invention, there is provided an x-ray inspection system comprising: an x-ray source, a sample support for supporting a sample to be inspected, an x-ray detector, a sample positioning assembly including a first positioning mechanism for moving the sample support along a first axis towards and away from the x-ray source, a proximity sensor fixed to the x-ray source configured to provide a measurement of distance between the x-ray source and a surface of a sample on the sample support, and a controller connected to the proximity sensor.

The controller may be connected to the sample positioning assembly and control the sample positioning assembly based on the measurement of distance from the proximity sensor. The controller may comprise an image processor and may use the measurement of distance from the proximity sensor in image processing calculations.

The proximity sensor may comprise a laser light source directing a laser beam parallel to the first axis. The proximity sensor may be a confocal sensor.

Providing a direct measurement of the distance between the x-ray source and the top surface of a sample is beneficial for several reasons, particularly in a high magnification system in which the top surface of the sample, which typically comprises the regions of interest, is brought very close to the x-ray source. First, the distance measurement can be used to calibrate the first positioning mechanism so that accurate positioning and subsequent image processing can be achieved. Second, the distance measurement can be used directly in a magnification calculation to provide an accurate measure of magnification. Third, the distance measurement or multiple distance measurements can be used to prevent any collision between the top surface of the sample and the x-ray source, which would likely be very damaging to both.

Advantageously the controller is configured to calibrate the first positioning mechanism based on distance measurements from the proximity sensor. In particular, the positioning assembly may comprise a linear encoder arranged along the first axis and the controller may be configured to calibrate linear encoder using one or more distance measurements from the proximity sensor.

The controller may be configured to perform a magnification calculation using the distance determined by the proximity sensor.

The positioning assembly may comprise a second positioning mechanism configured to move the sample support in a plane orthogonal to the first axis, and the controller may be configured to operate the second positioning mechanism so as to perform a scan of a top surface of a sample on the sample support relative to the proximity sensor. The scan may be a raster scan.

Advantageously, the controller is configured to record a closest point of the sample recorded during the scan. The controller may then be configured to calculate a closest safe position of the first positioning mechanism from the x-ray source based on the closest point; and control the first positioning assembly to prevent the first positioning assembly from being moved closer to the x-ray source than the calculated closest safe position.

The x-ray source is advantageously located above the sample support. The sample support may be configured to support a semiconductor wafer. The sample support may be configured in accordance with one of the eleventh to fifteenth aspects of the invention.

The x-ray source is preferably a sealed x-ray tube, with a transmission target, as described in relation to the first aspect of the invention.

The x-ray inspection system may further comprise a sample support position detection assembly comprising one or more laser interferometers positioned adjacent to the sample support and configured to detect a position or a change in position of the sample support, as described in more detail with reference to the fifth aspect of the invention.

The x-ray inspection system may comprise a detector positioning assembly for positioning the x-ray detector relative to the x-ray source, wherein the detector positioning assembly comprises a horizontal detector positioning mechanism for moving the detector in at least two non-parallel directions within a horizontal plane, and a detector tilting mechanism configured to allow the detector to be tilted from the horizontal plane about at least two non-parallel axes. Advantageous features of the detector positioning assembly are described in more detail with reference to the ninth and tenth aspects of the invention.

The system may be configured to perform a tomosynthesis calculation on images recorded by the x-ray detector.

In a seventh aspect of the invention, there is provided a method of controlling an x-ray inspection system, the x-ray inspection system comprising: an x-ray source; a sample support for supporting a sample to be inspected, wherein the sample support comprises a support surface; an x-ray detector; a sample positioning assembly including a first positioning mechanism for moving the sample support along a first axis towards and away from the x-ray source and a second positioning mechanism configured to move the sample support in a plane orthogonal to the first axis; and a proximity sensor fixed to the x-ray source for determining a distance between the x-ray source and a surface of a sample on the sample support, the method comprising:

a) placing a sample on the sample support;
b) positioning the sample support using the first positioning mechanism at a first position of the first positioning mechanism;
c) moving the sample support in a plane orthogonal to the first axis past the proximity sensor and recording the distance of a surface of the sample from the x-ray source at a plurality of positions as the sample support is moved in the plane;
d) calculating a closest safe position of the first positioning mechanism from the x-ray source based on the recorded distances; and
e) controlling the first positioning assembly to prevent the first positioning assembly from being moved closer to the x-ray source than the calculated closest safe position.

The method may further comprise performing a magnification calculation based on the recorded distances.

The step of moving the sample support may comprise moving the sample support in a raster scan configuration.

In an eighth aspect of the invention, there is provided a method of controlling an x-ray inspection system, the x-ray inspection system comprising: an x-ray source; a sample support for supporting a sample to be inspected, wherein the sample support comprises a support surface; an x-ray detector; a sample positioning assembly including a first positioning mechanism for moving the sample support along a first axis towards and away from the x-ray source and a second positioning mechanism configured to move the sample support in a plane orthogonal to the first axis; and a proximity sensor fixed to the x-ray source for determining a distance between the x-ray source and a surface of a sample on the sample support, the method comprising:

a) placing a sample on the sample support;
b) positioning the sample support using the first positioning mechanism at a first position of the first positioning mechanism;
c) recording the distance of a surface of the sample from the x-ray source at the first position; and
d) performing a magnification calculation based on the recorded distance.

In this context a "magnification calculation" is a calculation of the magnification of an image of the sample, or a portion of the sample, on the x-ray detector.

In a ninth aspect of the invention, there is provided an x-ray inspection system comprising: an x-ray source; a sample support for supporting a sample to be inspected, wherein the sample support comprises a support surface extending in a first horizontal plane; an x-ray detector; a sample positioning assembly for positioning the sample support relative to the x-ray source; a detector positioning assembly for positioning the x-ray detector relative to the x-ray source, wherein the detector positioning assembly comprises a horizontal detector positioning mechanism for moving the detector in at least two non-parallel directions within a second horizontal plane; and a detector tilting mechanism configured to allow the detector to be tilted from the second horizontal plane about at least two non-parallel axes.

The detector can then be positioned so that an imaging surface of the detector is always normal to a line between the centre of the detector and the x-ray source whatever the position of the detector in the second horizontal plane. Having the imaging surface of the detector always directly facing the x-ray source in every imaging position provides the highest quality of the resulting images, as it eliminates blurring that occurs when x-rays enter the detector at extreme oblique angles.

Advantageously, the two non-parallel axes are coplanar. The x-ray detector may comprise a planar imaging surface, and the two non-parallel axes may also lie in the same plane as the imaging surface. This arrangement simplifies image processing calculations, particularly when the images are to be used in a tomosynthesis algorithm.

Advantageously, the tilting mechanism is driven independently of the horizontal detector positioning mechanism. This allows for very accurate orientation of the detector. The tilting mechanism may comprise a first gimbal and a second gimbal. In a preferred embodiment, the first gimbal is driven by a first gimbal motor and the second gimbal is driven by a second gimbal motor. The first and second gimbal motors may be automatically controlled by a single controller. The controller may be configured to control the first and second gimbal motors to position the x-ray detector in a plurality of imaging positions to generate a plurality of images that can be combined in a tomosynthesis calculation. The first and second gimbal motors may comprise direct read encoders on an output side.

The x-ray inspection system may further comprise a controller, the controller connected to and configured to control the detector positioning assembly, the controller configured to move the detector to a plurality of imaging positions and to control the tilting mechanism to ensure that an imaging surface of the detector is normal (i.e. perpendicular) to a line between a centre of the detector and the output spot of the x-ray source in each of the plurality of imaging positions.

The controller may be configured to control the horizontal detector positioning mechanisms to move the detector in a raster scan pattern in a horizontal plane.

The sample positioning assembly may comprise a vertical sample positioning mechanism for moving the sample support in a vertical direction, orthogonal to the horizontal plane. The sample positioning assembly may comprise a first horizontal sample positioning mechanism for moving the sample support in a first horizontal direction, and a second horizontal sample positioning mechanism for moving the sample support in a second horizontal direction. Advantageous features of the sample positioning assembly are described in relation to the fourth aspect of the invention. In particular, the second horizontal sample positioning mechanism may be mounted on the vertical sample positioning mechanism and the vertical positioning mechanism mounted on the first horizontal sample positioning mechanism.

The sample support may be configured to support a semiconductor wafer. The sample support may be configured in accordance with one of the eleventh to fifteenth aspects of the invention.

The x-ray inspection system may further comprise a frame to which the sample positioning assembly and the detector positioning assembly are mounted, wherein the x-ray source is fixed to the frame.

The x-ray source is advantageously positioned above the sample support.

The system may be configured to perform a tomosynthesis calculation on images recorded by the x-ray detector.

The x-ray source is preferably a sealed x-ray tube, with a transmission target, as described in relation to the first aspect of the invention.

The x-ray inspection system may further comprise a sample support position detection assembly comprising a non-contact position measuring device, such as a laser interferometer positioned adjacent to the sample support and configured to detect a position or a change in position of the sample support, as described in more detail with reference to the fifth aspect of the invention.

The x-ray inspection system may further comprise a proximity sensor fixed to the x-ray source for determining a distance between the x-ray source and a surface of a sample on the sample support, as described in more detail with reference to the sixth, seventh and eighth aspects of the invention.

In a tenth aspect of the invention, there is provided a method of controlling an x-ray inspection system, the system comprising an x-ray source, a sample support for supporting a sample to be inspected, wherein the sample support comprises a support surface extending in a first horizontal plane, an x-ray detector, a sample positioning assembly for positioning the sample support relative to the x-ray source, a detector positioning assembly for positioning the x-ray detector relative to the x-ray source, wherein the detector positioning assembly comprises a horizontal detector positioning mechanism for moving the detector in at least two non-parallel directions within a second horizontal plane, and a detector tilting mechanism configured to allow the detector to be tilted from the second horizontal plane about at least two non-parallel axes, the method comprising:
    controlling the detector positioning assembly to move the detector to a plurality of imaging positions and to controlling the tilting mechanism to ensure that the detector is facing the x-ray source in each of the plurality of imaging positions.

As described, having the imaging surface of the detector always directly facing the x-ray source in every imaging position provides the highest quality of the resulting images as blurring that results from x-rays entering the detector at an oblique angle is eliminated.

In an eleventh aspect of the invention, there is provided a sample support for a semiconductor wafer comprising:
    a generally planar support surface having an imaging area configured to support a semiconductor wafer; and
    at least one depression in the imaging area of the support surface in fluid communication with a vacuum port, wherein the sample support has a thickness in a direction normal to the planar support surface and wherein the rate of change of thickness of the sample support has a maximum value of no more than 5% per millimeter of travel across the imaging area.

In this context the term vacuum port means an outlet to which a vacuum source can be connected. The application of a vacuum to the vacuum port creates low pressure in the depression or depressions underneath a wafer on the sample support, thereby holding the wafer in place. This is how conventional wafer chucks work.

The depression may have a sidewall. The sidewall preferably extends in a continuous curve from a first side of the depression to an opposite side of the depression. Advantageously, the sidewall has a minimum radius of curvature of at least 10 mm, and more preferably at least 15 mm. The minimum radius of curvature is preferably at least one order of magnitude, and preferably at least two orders of magnitude, greater than the maximum depth of the depression below the planar support surface. A transition region between the planar support surface and the sidewall of the depression may extend in a continuous curve and advantageously has a minimum radius of curvature of no less than 1 mm.

Preferably a maximum rate of change of depth of the depression with relative to the planar support surface is no more than 0.2 mm per mm of travel across the depression parallel to the planar support surface.

Advantageously, the thickness of the sample support varies by no more than 10% of the maximum thickness across the imaging area, and more preferably varies by no more than 5% across the imaging area. Advantageously, a minimum distance from a first side of the depression to an opposite side of the depression is at least 10 times the maximum depth of the depression and preferably at least 20 times the maximum depth of the depression.

Advantageously, the sample support is formed from a homogenous, non-crystalline material, which does not give rise to significant contrast variations in x-ray images of the sample support but is mechanically robust. Preferably, the sample support has a density of less than 2000 kg/m$^3$ and more preferably less than 1500 kg/m$^3$. Suitable materials include polyether ether ketone (PEEK), beryllium, and acetal.

The benefit of a sample support in accordance with this aspect of the invention is that it does not give rise to significant contrast changes in x-ray images resulting from x-rays that have passed through the support. Advantageously, changes in the thickness of the wafer support as a result of the depressions are gradual, are small compared to the overall thickness of the support, and do not include any sharp edges.

The sample support may comprise a plurality of depressions within the imaging area. Each depression may be substantially annular. The radial width of each depression may be between 2 and 10 mm. The maximum depth of each depression below the planar support surface may be between 0.1 and 0.5 mm.

The vacuum port may be positioned in an area outside of an imaging area of the support.

In a twelfth aspect of the invention, there is provided a sample support for a semiconductor wafer comprising: a generally planar support surface having an imaging area configured to support a semiconductor wafer; and at least one depression in the imaging area of the support surface in fluid communication with a vacuum port, wherein the depression has a curved sidewall that extends from a first side of the depression to an opposite side of the depression.

Preferably, the sidewall extends in a continuous curve from the first side of the depression to the opposite side of the depression.

Advantageously, the sidewall has a minimum radius of curvature of at least 10 mm, and more preferably at least 15 mm. The minimum radius of curvature is preferably at least 2 orders of magnitude greater than the maximum depth of the depression below the planar support surface.

In a thirteenth aspect of the invention, there is provided a sample support for a semiconductor wafer comprising:
a generally planar support surface having an imaging area configured to support a semiconductor wafer; and
at least one depression in the imaging area of the support surface in fluid communication with a vacuum port,
wherein a maximum rate of change of depth of the depression with relative to the planar support surface is no more than 0.2 mm per mm of travel across the depression parallel to the planar support surface.

In a fourteenth aspect of the invention, there is provided a sample support for a semiconductor wafer comprising:
a generally planar support surface having an imaging area configured to support a semiconductor wafer; and
at least one depression in the imaging area of the support surface in fluid communication with a vacuum port,
wherein the sample support has a thickness in a direction normal to the planar support surface and the thickness of the sample support varies by no more than 10% of the maximum thickness across the imaging area, and more preferably varies by no more than 5% across the imaging area.

In a fifteenth aspect of the invention, there is provided a sample support for a semiconductor wafer comprising:
a generally planar support surface having an imaging area configured to support a semiconductor wafer; and
at least one depression in the imaging area of the support surface in fluid communication with a vacuum port,
wherein a minimum distance from a first side of the depression to an opposite side of the depression is at least 10 times, and preferably at least 20 times, the maximum depth of the depression.

In a sixteenth aspect of the invention, there is provided an x-ray inspection system comprising an x-ray source, an x-ray detector, and a sample support in accordance with any one of the eleventh to fifteenth aspects positioned between the x-ray source and the x-ray detector.

The system may be configured to perform a tomosynthesis calculation on images recorded by the x-ray detector.

The x-ray source may be located above the sample support. The x-ray inspection system may comprise a cabinet, the cabinet containing the x-ray source, the sample support and the x-ray detector; and an air mover configured to force air into the cabinet through an air inlet in the cabinet above the sample support, wherein the air mover and cabinet are configured to force air through the cabinet from the air inlet past the sample holder to an air outlet in the cabinet below the sample holder.

Features described in relation to one aspect of the invention may be applied to other aspects of the invention. Any combinations of two or more of the aspects of the invention are contemplated within this disclosure.

BRIEF DESCRIPTION OF THE DRAWINGS

Embodiments of the invention will now be described in detail, by way of example only, with reference to the accompanying drawings, in which.

DETAILED DESCRIPTION

X-Ray Inspection System Components

Figure 1:
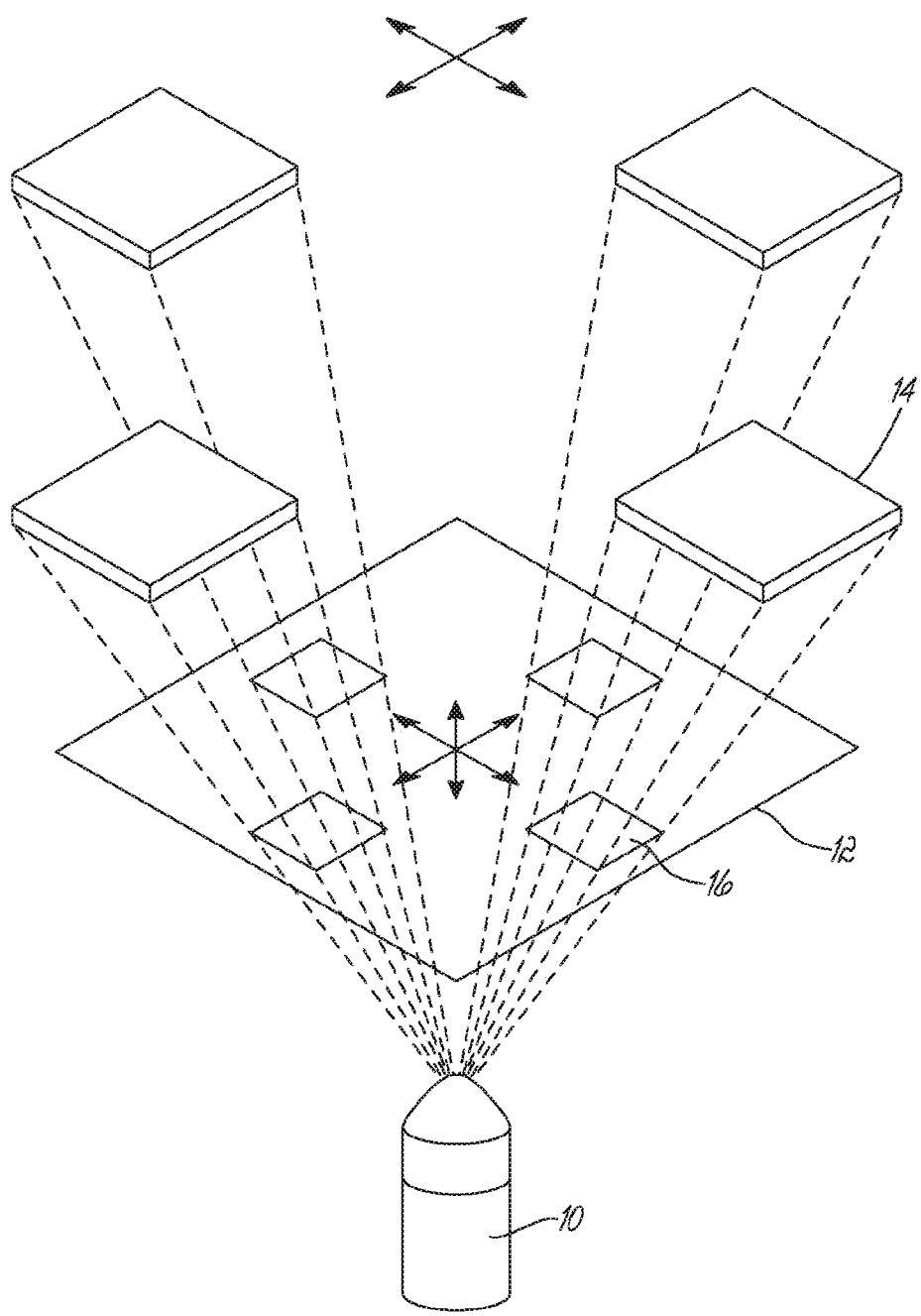
FIG. 1 is a schematic illustration of the basic components of an x-ray inspection system.

FIG. 1 is a schematic illustration of the basic elements of an x-ray imaging system. The system shown in FIG. 1 comprises an x-ray source 10, which in this system is held stationary, a moveable sample support 12 and a moveable detector 14. X-rays from the x-ray source 10 pass through the support and any sample mounted on the sample support, and impinge on the detector 14. FIG. 1 illustrates the areas 16 on the sample support corresponding to the field of view of the detector 14. The field of view of the detector is selected by a user by the relative positioning of the detector 14, sample support 12 and x-ray source 10 so that the sample, or an area of the sample, is within the field of view of the detector. The detector can move to different imaging positions so that different projections can be taken through samples on the sample support. In this context, a different projection means that the x-rays pass through the sample on the support in a different direction.

Typically there are 2 operation modes. In a first mode the detector stays stationary and the sample support is moved to different locations to acquire different fields of view. In a second mode, the detector and sample support are moved in a co-ordinated manner to get a different angular projection through the same field of view. This coordinated motion enables three dimensional reconstructions to be generated using tomosynthesis.

The support 12 is moveable in the XY plane in order that the sample on the support can be moved to a position between the x-ray source and the detector. In the example shown in FIG. 1, the support 12 is also moveable in a vertical or Z-direction. This allows the magnification of the detected image at the detector to be adjusted. In other words, larger or smaller areas of the support can be made to fall within the field of view of the detector depending on the relative distance between the x-ray source 10 and the support 12 and the x-ray source 10 and the detector 14. As explained, the area of the sample to be imaged must fall within the field of view.

Generally, the x-ray source 10 includes a tube that generates the beam of x-rays by accelerating electrons from an electron gun and causing the energetic electrons to collide with a metal target. The x-rays contained in the beam are sufficiently energetic to penetrate through the thickness of target objects on the sample support 12 so that attenuated x-rays reach the detector 14. The differential levels of x-ray attenuation by the materials of different density in the sample and their different thicknesses, within the region being imaged produces contrast in the resulting image captured by the detector.

The detector 14 may be a digital detector and have a construction as is well known in the art. Generally, the detector includes an active area, a sensor that converts the incoming x-rays over the active area into another signal type that can be measured or imaged, and an amplifier used to boost the amplitude of the signals. The signals are converted from an analogue form to a digital form within the detector 14 and a digital image is output from the detector. An exemplary digital detector is a complementary metal oxide semiconductor (CMOS) flat panel detector that includes a two dimensional pixel array of silicon photodiodes constituting the active area.

Tomosynthesis

In FIG. 1, the detector 14 is shown in four different positions and there are four corresponding regions 16 on the support. It should be understood that many more positions are possible. In a tomosynthesis system, a three dimensional model of the area of the sample being imaged may be constructed from any number of projections, and anything between 12 and 720 projections is used in practice.

The resulting three dimensional model allows a user to inspect any plane through the imaged area, and to review a three dimensional image to find defects such as voids.

Various tomosynthesis algorithms and processing techniques are known in the art, such as the ReconPro reconstruction solution offered by Prexion Inc. of 411 Borel Avenue, Suite 550, San Mateo, Calif. 94402, USA.

A requirement for generating a three dimensional model using a plurality of images is a knowledge of the precise spatial relationship between x-ray source, region of interest and detector for each image. The way in which the two-dimensional images are combined in tomosynthesis relies on this geometric information, as it is required in the mathematical formulas that are used.

Clean Room X-Ray Inspection System

In order to use a system as described above to inspect and generated models of samples that are produced in a clean room environment, such as semiconductor wafers, during production, it is necessary that the x-ray inspection system itself meets clean room standards.

Figure 2:
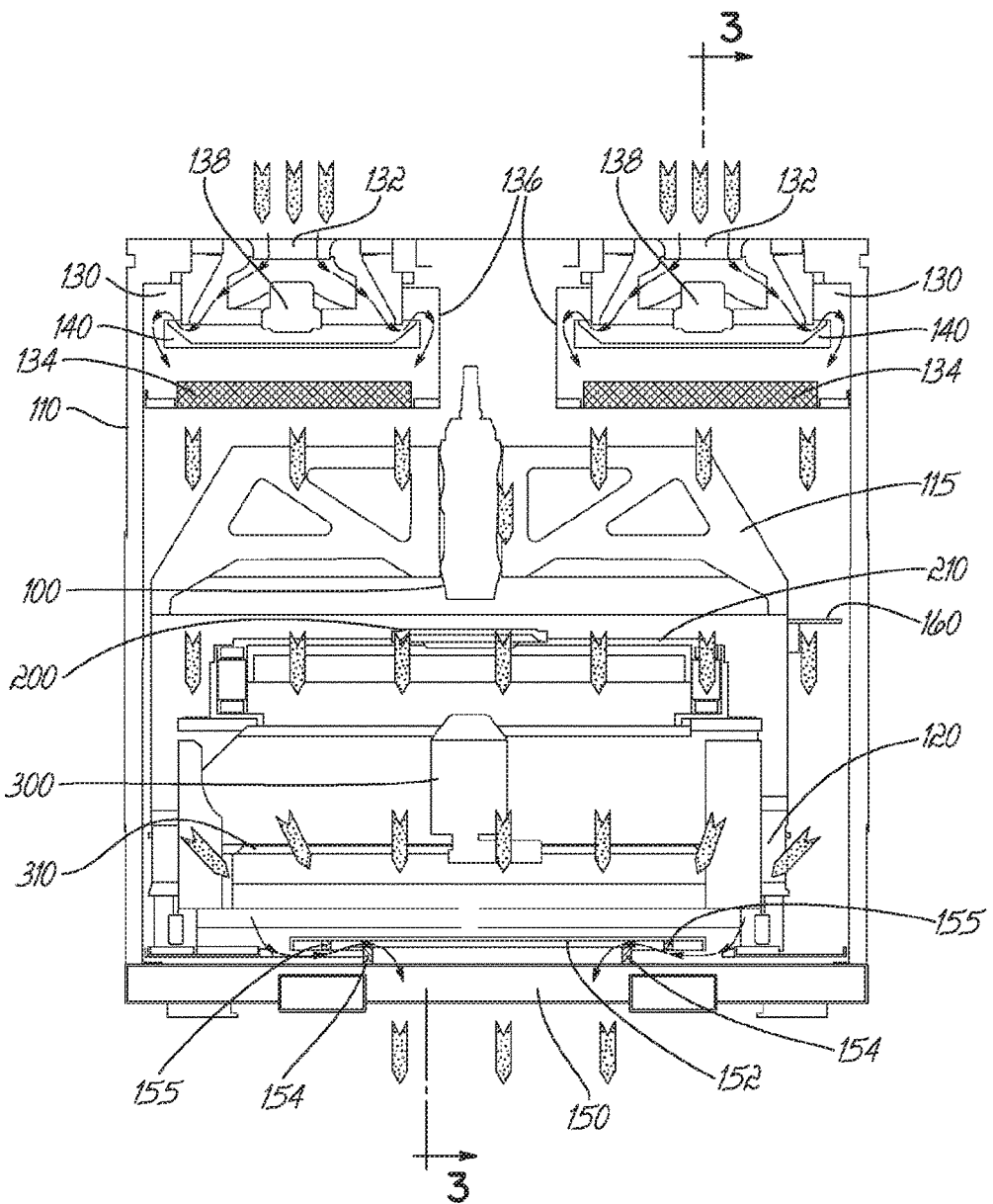
FIG. 2 is a first schematic cross-section illustration of an x-ray inspection system in accordance with the invention.
Figure 3:
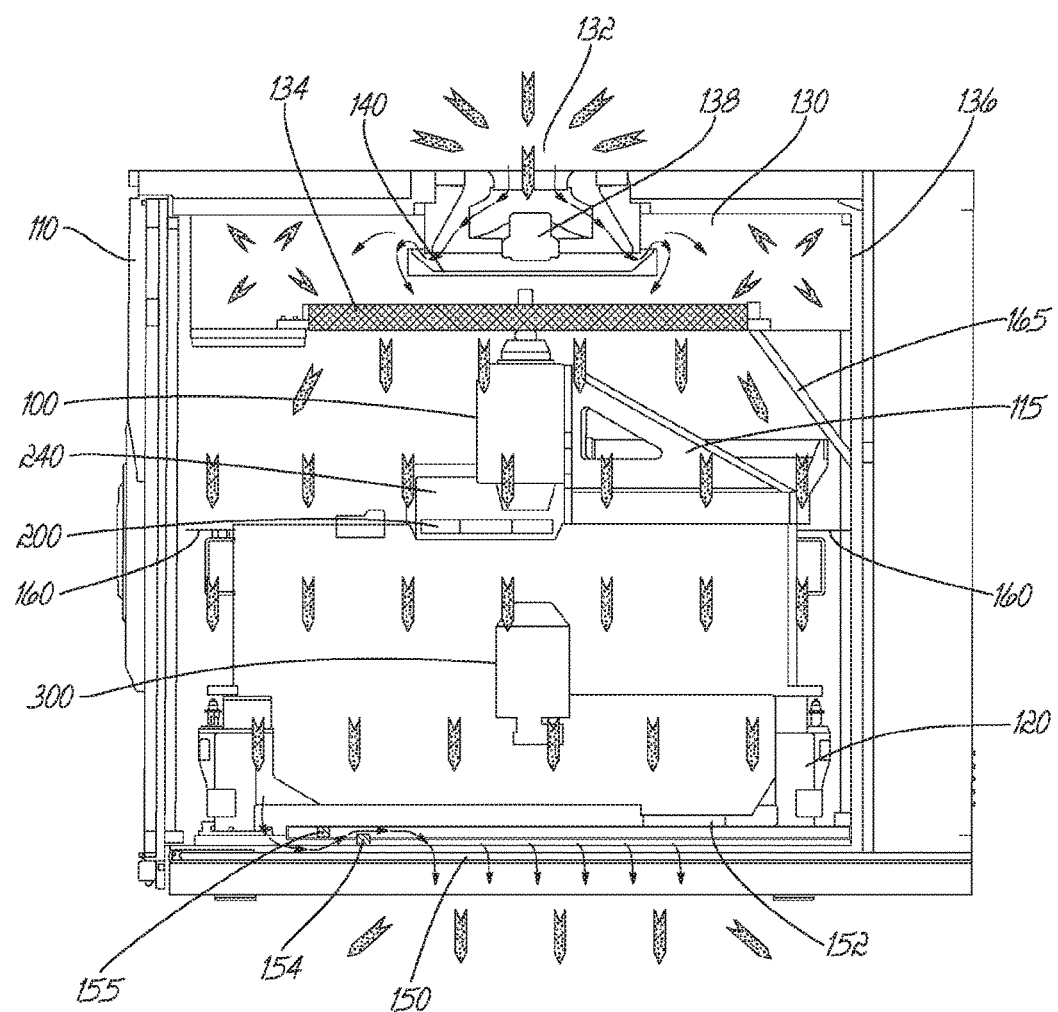
FIG. 3 is a second schematic cross-section illustration of the x-ray inspection system of FIG. 2 along plane A-A in FIG. 2.
Figure 4:
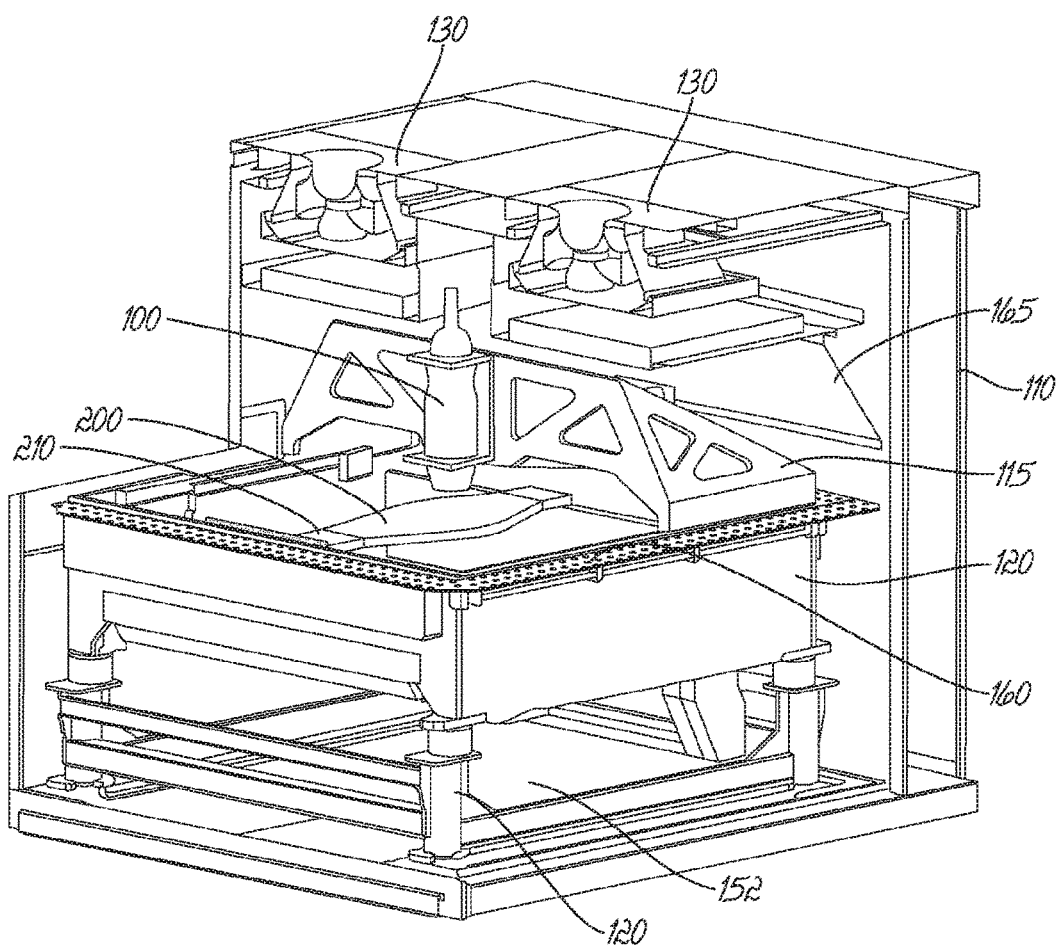
FIG. 4 is a simplified perspective view of a system of the type shown in FIG. 2, with the cabinet removed.

FIG. 2 is a schematic cross section of an x-ray inspection system in accordance with one embodiment of the invention. FIG. 3 is a second cross section of the system shown in FIG. 2, taken perpendicular to the cross section of FIG. 2 along plane A-A. FIG. 4 is a partially cut-away perspective view of the system of FIGS. 2 and 3.

The system illustrated in FIGS. 2, 3 and 4 comprises an x-ray tube 100, a sample support 200 and a detector 300, within a cabinet 110. The cabinet 110 is lead lined to provide a shield from x-rays generated by the x-ray tube 100.

Within the cabinet 110 there is a supporting frame 120, on which the x-ray tube 100, sample support 200 and detector are all mounted. The sample support 200 is configured to hold a semiconductor wafer (not shown in FIG. 2, 3 or 4).

Figure 15:
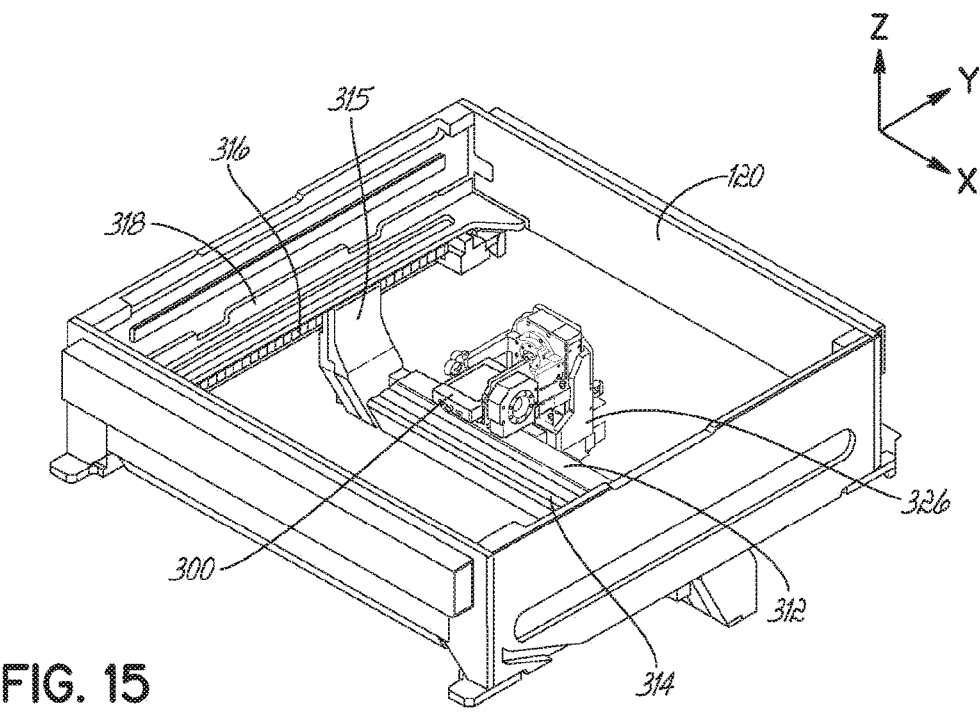
FIG. 15 is an illustration of a mechanism to move the x-ray detector in the horizontal plane.
Figure 16:
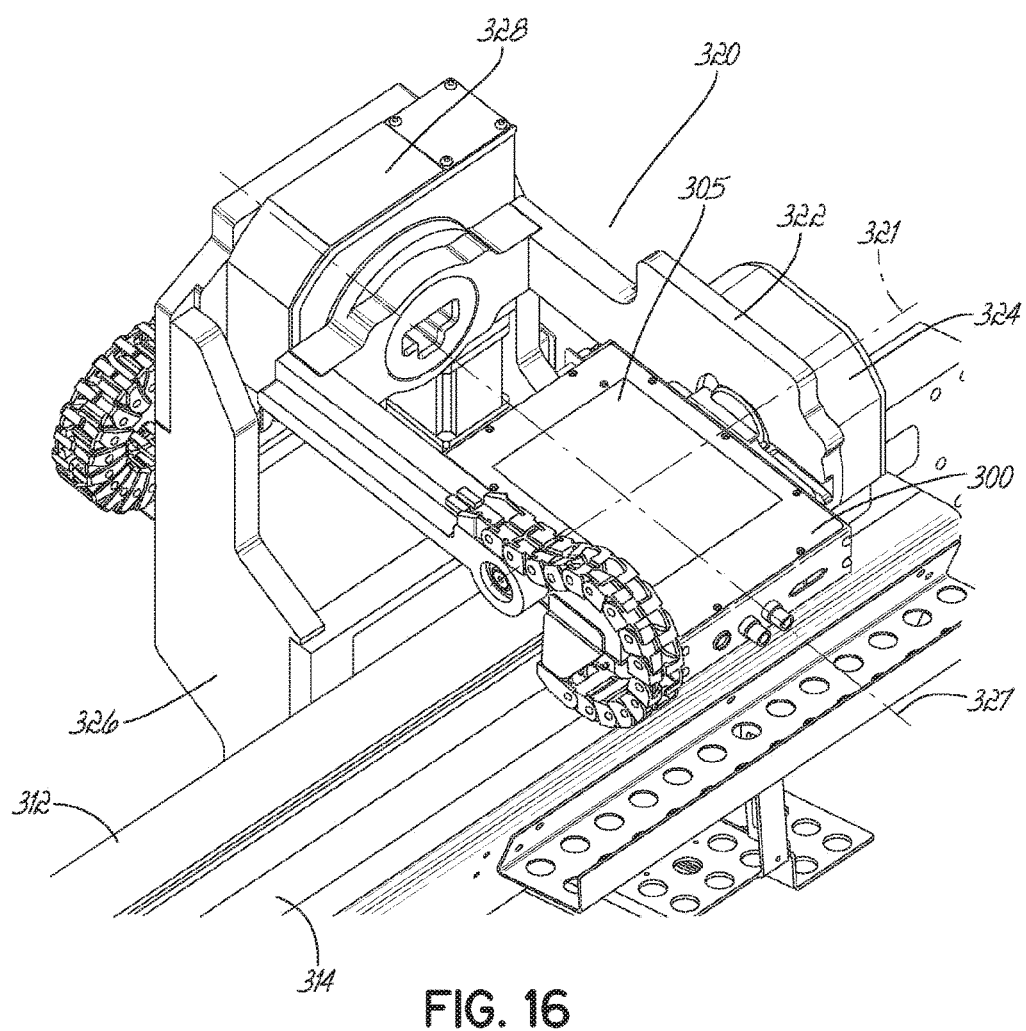
FIG. 16 is a perspective view of the detector tilting mechanism.

The frame comprises a detector positioning assembly 310 (not visible in FIG. 3 or 4) that allows the detector 300 to move to in a horizontal plane. The detailed components of the detector positioning stage 310 are not shown in the FIGS. 2 and 3 and any suitable arrangement may be used for a clean room compatible system. However, one inventive and advantageous arrangement is described in detail with reference to FIGS. 14-16. In this embodiment the detector positioning mechanism comprises a first beam 314, extending along the X-axis, on which the detector is supported and the supporting frame 120 having a rail 318 extending in the Y-direction, on which the first rail 314 is supported. Linear motors are provided to allow the detector to be moved along the beam 314 and to allow the beam 314 to be moved along the rail 318. In this manner the detector can be moved to any position within a horizontal plane (within the frame). A tilting mechanism is also provided that allows the active area of the detector to be oriented to face the x-ray source in all imaging positions. The tilting mechanism is shown in FIG. 16 and will be described in more detail later on in the specification. The detector in this embodiment is a CMOS flat panel detector, such as the Dexela 1512 NDT, available from Dexela Limited, Wenlock Business Centre, 50-52 Wharf Road, London, N1 7EU, United Kingdom.

A sample positioning stage 210 is provided on the supporting frame above the detector positioning stage 310. The detailed components of the sample positioning stage are shown in and described with reference to FIGS. 6 and 7. However, sample support positioning arrangements having a different geometry or layout may be used to provide a clean room compatible system. In this embodiment, the sample positioning stage comprises a similar arrangement of motors and rails as the detector positioning stage for moving the sample support 200 in a horizontal plane, with the addition of a further motor to move the sample support in a vertical direction, towards and away from the x-ray tube. This allows for the magnification of the images to be selected. The sample positioning stage is described in more detail below with reference to FIGS. 6 and 7.

A sample input shutter 240 as shown in FIG. 3, is provided to allow a sample, such as a semiconductor wafer, to be loaded onto the sample support 200. The shutter is provided in the cabinet and has a pneumatically operated mechanism. The shutter is lead lined and sealed by steel labyrinth bars to prevent escape of x-rays. The shutter is automatically opened when inspection of a wafer is complete to enable unloading of the completed wafer and reloading of a new wafer. The wafer load/unload is handled by an Equipment Front End Module (EFEM) unit to provide a continuous clean environment for the wafer as it is moved from a Front Opening Unified Pod (FOUP) to the sample support. A FOUP is a special plastic enclosure designed to hold silicon wafers securely and safely in a clean room environment, and to allow the wafers to be removed for processing or measurement by tools equipped with appropriate load ports and robotic handling systems. The EFEM used in this embodiment is a Brooks JET™ Atmospheric Transport System unit, available from Brooks Automation, Inc., 15 Elizabeth Drive, Chelmsford, Mass. 01824, U.S.A.

The x-ray tube 100 is fixed to an x-ray tube bracket 115 and is positioned above the sample support 200 and the detector 300. The x-ray tube bracket 115 is provided on the frame 120 above the sample positioning stage. The x-ray tube cannot move relative to the frame 120.

In this embodiment, the x-ray tube 100 is a sealed-transmissive type of x-ray tube, such as the NT x-ray tube from Dage Holdings Limited, 25 Faraday Road, Rabans Lane Industrial Area, Aylesbury, Buckingham HP198RY United Kingdom. This type of x-ray tube provides for a very long service lifetime, typically more than 5000 hours of operation before maintenance is required, as well as very high resolution imaging. A sealed-transmissive type of x-ray tube comprises a fully sealed vacuum tube and a transmission target forming a portion of the exterior wall of the tube. The transmission target is constructed so that electrons impinge on a first side of the target facing towards the interior of the tube and at least some of the x-rays generated are emitted through a second side of the target facing outwardly from the tube. This is sometimes referred to as an end window transmission tube.

An end window transmission tube allows for the generation of an x-ray source with small spot size and allows the sample being imaged to be brought close to the x-ray source. This means that high magnification and high resolution images can be obtained. By arranging the x-ray tube 100 above the sample support 200 and configuring the sample support to support a semiconductor wafer between the sample support and the x-ray tube, the surface of the semiconductor wafer can be brought very close to the x-ray source, allowing for high magnification images to be obtained within a compact system.

A pair of fan filter units (FFUs) 130 is mounted to the cabinet above the sample support. The FFUs are configured to draw air in through respective air inlets 132 in the ceiling of the cabinet and drive the air through a HEPA filter plate 134 in each FFU, downward past the sample support 200 to an air outlet 150 in the floor of the cabinet. The direction of the airflow is indicated by the arrows in FIGS. 2 and 3.

In this example, each FFU 130 comprises an enclosure 136, a fan 138 configured to draw air into the enclosure through an air inlet 132 on one face of the enclosure and out through an outlet covered by a HEPA filter plate 134. Each FFU is constructed so that when the fan 138 is running, the air pressure within the enclosure 136 is higher than outside the enclosure. This helps to provide a uniform flow of air through the filter plate 134, and minimises local flow rate variations.

In this embodiment each FFU 130 also comprises an internal shield 140 positioned between the fan and the filter plate, which is not a feature of standard FFUs. This shield 140 has two functions. It is both an x-ray absorber and an airflow baffle. However, two separate components could be used, one for each of these functions. The shield 140 is a lead lined steel tray that is larger than and spans the air inlet 132 of the FFU 130 so that x-rays from the x-ray tube 100 cannot escape through the air inlet 132. The airflow path past the shield 140 and out of the FFU 130 is made labyrinthine. The shield also forces air from the fan 138 to the outer edges of the enclosure 136, as is clearly illustrated in FIGS. 2 and 3. This promotes a uniform air flow through the filter plate 134.

The air flow through the cabinet from the filter plates 134 past the sample support 200 is laminar. There is no recirculation of air from below the sample support 200 to a position above the sample support. The use of HEPA filters 134, laminar airflow and ensuring that there are no moving parts in the system between the filter plates 134 and the sample support 200, means that there is minimal risk of any dust or other particulates from becoming airborne, or falling from above, and landing on, and thereby contaminating or damaging, the semiconductor wafer on the sample support 200.

In order to ensure that there is no recirculation of air from below the sample support 200 to above the sample support, a perforated deck 160 (best seen in FIG. 4) is provided at the level of the sample support. The perforated deck 160 is positioned at the same height as an uppermost position of the sample support 200, corresponding to the highest magnification of the system. The perforated deck 160 allows air from above the deck to pass to beneath the deck, but creates a small pressure difference across the deck so that there is higher air pressure above the deck than below the deck. The perforated deck restricts the air flow path of the air by approximately 50%. This restriction increases the pressure of the air above the deck. This small pressure difference substantially prevents recirculation of air to above the deck, as air will naturally flow from an area of high pressure to an area of low pressure. A baffle plate 165, as shown in FIG. 3, is also provided to promote laminar air flow.

Figure 5A:
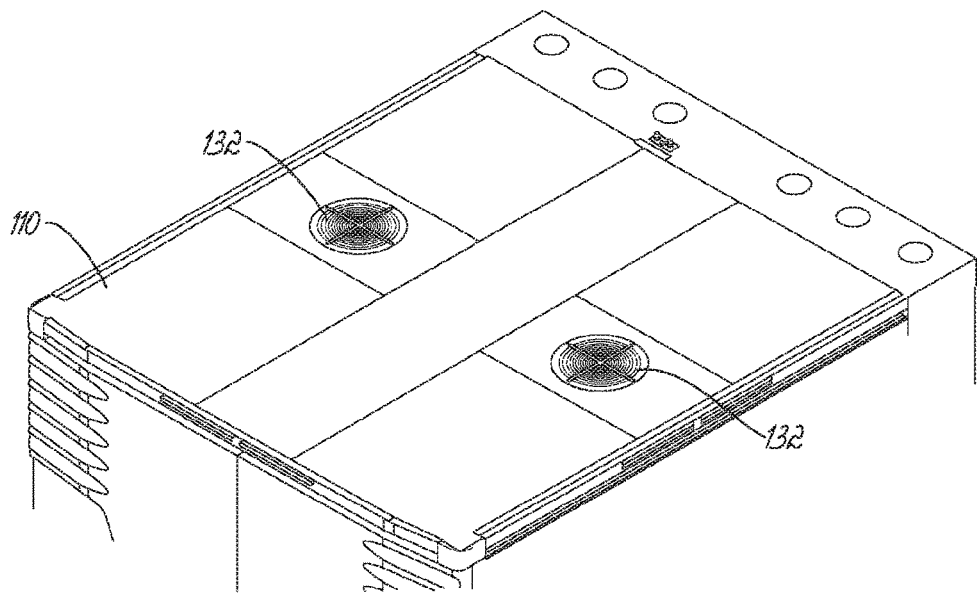
FIG. 5a is a perspective view of the top of the cabinet of FIG. 4.
Figure 5B:
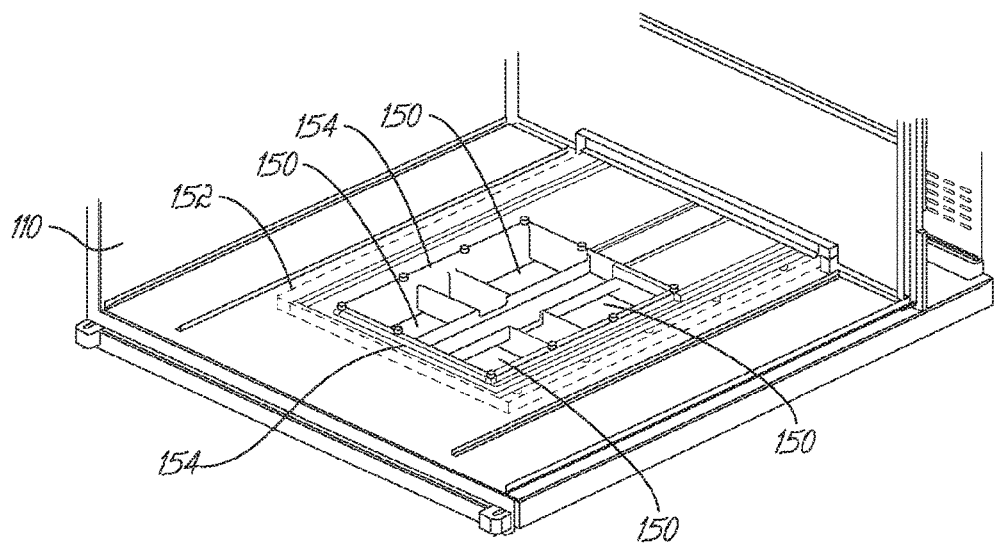
FIG. 5b is a cut-away view of the base of the cabinet shown in FIG. 4.
Figure 5C:
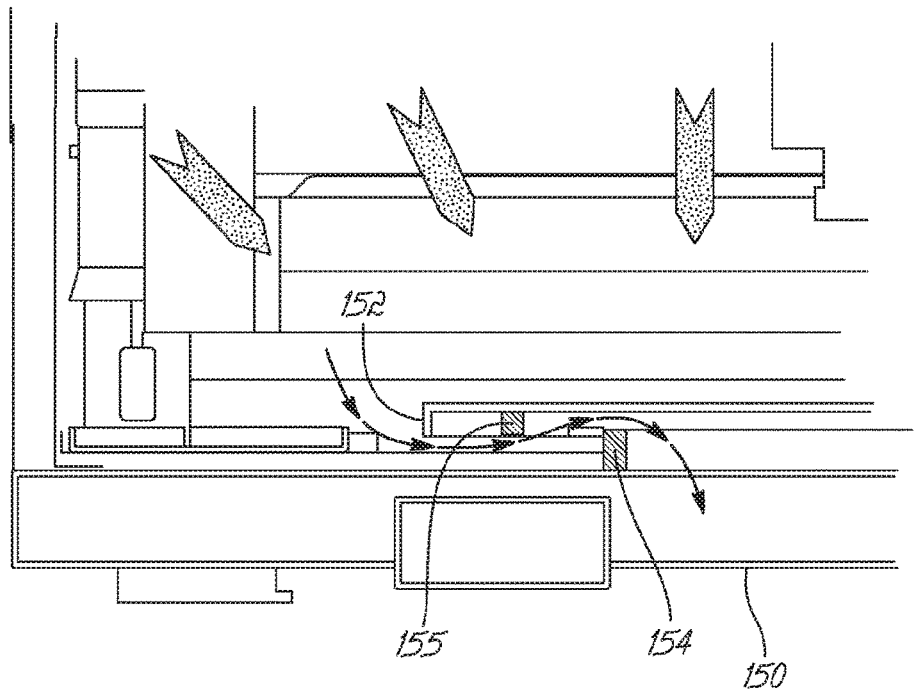
FIG. 5c is close-up view of the air flow through the outlet as shown in FIG. 2.

The air outlet 150 in the floor of the cabinet is relatively large compared with the air inlets 132, again to promote laminar airflow and reduce any recirculation of air upward. FIG. 5a shows the top of the cabinet. The air inlets 132 can be seen, allowing air to be drawn into the FFUs. FIG. 5b is a cut-away view of the air outlet in the bottom of the cabinet. The air outlet 150 comprises four separate openings. The openings are surrounded by steel blocks 154. The spaces between the four outlet openings are provided to accommodate electrical cabling for providing power and data to and from the cabinet. The air outlet is covered by an outlet shielding plate 152 (shown in FIG. 5b transparent and in dotted outline) to prevent the escape of x-rays from the cabinet. The function of the outlet shielding plate 152 is best shown in FIG. 5c. The outlet shielding plate 152 is lead lined to absorb x-rays. Steel blocks 155 are also provided on the underside of the shielding plate as x-ray absorbers within the air flow path to the outlet. The steel blocks 154 and 155 absorb x-rays and are positioned so that the air flow path to the outlet is made labyrinthine. This ensures that no x-rays can escape the cabinet through the air outlet.

In operation the FFUs 130 continuously force air through the cabinet to ensure that no dust or debris produced as a result of the operation of the sample positioning assembly and detector positioning assembly can reach samples on the sample support 200. The FFUs provide for at least a class 4 ISO 14644-1 clean roon environment within the cabinet. The FFUs operate throughout the movement and operation of the sample support 200 and detector 300, and as the samples are loaded and unloaded from the system. A system as described with reference to FIGS. 2, 3 and 4 should be able to operate for thousands of hours without requiring maintenance.

Sample Positioning

An exemplary sample positioning assembly will now be described in detail with reference to FIGS. 6 and 7.

The sample positioning assembly is used to position samples relative to the x-ray source so that images of desired regions of interest within the sample and different projections of regions of interest can be obtained. The x-ray source is positioned above the sample support and is static. It is therefore desirable to be able to move the sample support in the XY plane, which is the horizontal plane, to provide different projections and images of different regions of the sample. It is also desirable to move the sample support in the Z-direction, which is the vertical direction, towards and away from the x-ray source, to alter the magnification of the images. In particular, for semiconductor wafers there is a need to bring the wafer very close to the x-ray source so that very high magnification images can be produced while keeping the overall height of the system within a standard ceiling height and allowing the system to be reasonably easily transportable.

In operation, when obtaining a set of different projections for a tomosynthesis calculation, the sample needs to be moved in the X- and Y-directions more often than in the Z-direction. Once the image magnification is set for a sample, then the sample need only be moved in the X- and Y-directions to obtain the different projections.

In order that the x-ray inspection process does not become a bottleneck within a wafer processing plant, the inspection process needs to be fast. This means that the mechanism for moving the sample in the X- and Y-directions needs to be fast. It also needs to be accurate, particularly at very high magnification, in order to produce high resolution three dimensional models, as discussed.

In this embodiment, the sample positioning assembly is configured to move in raster scan pattern between imaging positions as a line by line collection of images along parallel lines, with these parallel scan lines extending in the X-direction. The X direction is indicated by the X arrow shown in FIGS. 6 and 7. This means that X-direction movement mechanism will have the highest amount of travel, and therefore should be fast so as to increase the overall speed of the process for collecting the x-ray images that are needed. For this reason, in this embodiment, the X-axis drive mechanism is coupled directly to the sample support, which means that the X-axis drive mechanism moves minimal mass comprising only the sample support and the moving portions of x-axis drive mechanism. Most importantly, the X-axis drive mechanism does not support or carry either the Y-axis drive mechanism or Z-axis drive mechanism and this enables the X-axis drive mechanism to move more quickly. Because the Z-axis drive mechanism is used relatively infrequently and does not need to be as fast as the X-axis and Y-axis drive mechanisms, it can be made with a relatively lower mass than the X-axis and Y-axis mechanisms. The Z-axis drive mechanism is positioned to support the X-axis drive mechanism and moves both the X-axis drive mechanism and the sample support in the Z-axis. The Y-axis drive supports the Z-axis drive mechanism and so moves the Z-axis drive mechanism, the X-axis drive mechanism and the sample support in the Y-axis direction. The Y-axis drive mechanism is mounted to a supporting frame, to which the x-ray source is also mounted.

Figure 6:
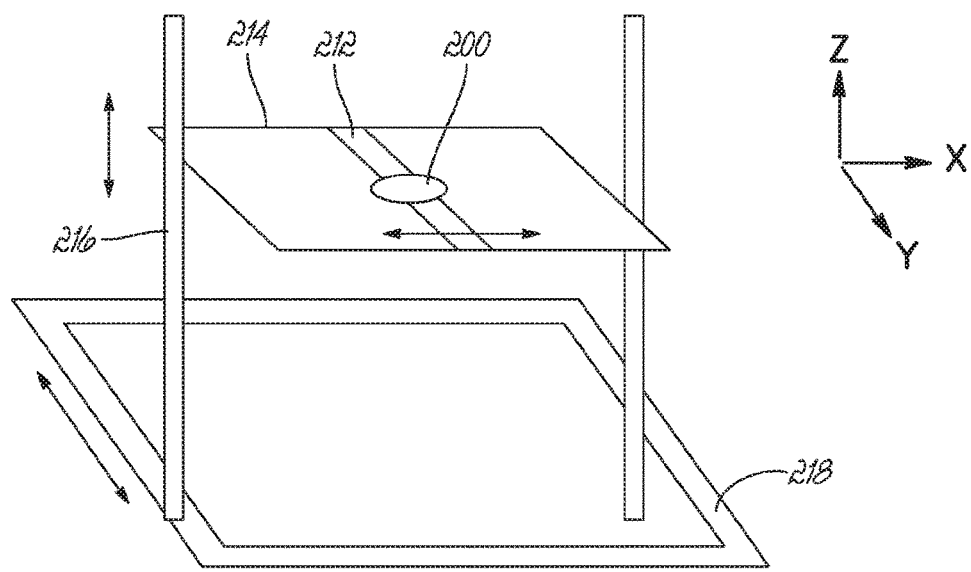
FIG. 6 is a schematic illustration of the arrangement of a sample positioning assembly in the x-ray inspection system of FIG. 2.

This arrangement is illustrated schematically in FIG. 6. The sample support 200 is mounted on a shuttle 212. The shuttle moves in the X-direction on a first frame 214. The shuttle 212 and frame together form the X-axis drive mechanism. The first frame 214 is mounted on a track 216 and can move up and down the track 216. The track 216 and first frame 214 together form a Z-axis drive mechanism. The track 216 is mounted on a second frame 218 and can move along the second frame 218 in the Y-direction.

Figure 7:
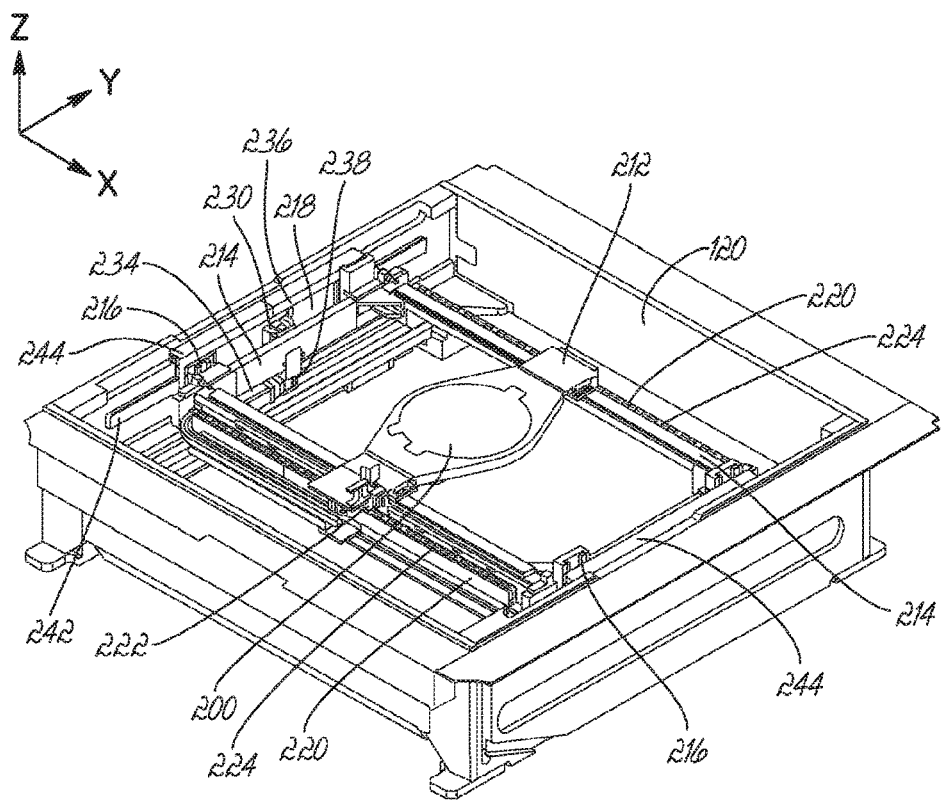
FIG. 7 is a perspective view of a sample positioning assembly in accordance with one aspect of the invention.

FIG. 7 illustrates one embodiment of this arrangement in more detail, in a system as shown in FIGS. 2, 3 and 4. In FIG. 7 it can be seen that the sample support 200 is configured to support a circular semiconductor wafer. The sample support is mounted to a first pair of linear motors 220. Each linear motor comprises a track of permanent magnets 224 extending in the X-direction and a coil assembly 222 that travels along the track in response to electrical control signals. Linear motors of this type are available from Aerotech, Inc., 101 Zeta Drive, Pittsburgh, Pa. 15238, USA. The linear motors 220 are mounted on a first frame 214. The first pair of linear motors 220 on the first frame form part of the X-axis drive mechanism.

The first frame 214 is mounted on a pair of lead screws 230, on opposite sides of the first frame 214, only one of which is visible in FIG. 7. Each lead screw 230 is driven by a rotary motor 234 through an angular gearbox 238. The lead screws 230 are each mounted to a plate 218 and move the first frame 214, together with the X-axis drive mechanism, up and down in the Z-axis direction relative to the plates 218. Four guide rails 216 are provided at the corners of the first frame 214 to support the first frame 214 and keep it stable as the first frame is moved in the Z-axis direction by the lead screws 230. The lead screws 230, associated rotary motors 234, gear boxes 238 and guide rails 216 form part of the Z-axis drive mechanism. A linear encoder 236 is provided between the first frame 214 and the plate 218 to determine and allow control of the vertical position of the first frame 214 and wafer support 200.

The plates 218 slide along guides 242 formed on the supporting frame 120. A second pair of linear motors 244 is connected between the plates 218 and the supporting frame 120 to move the plates 218, together with the Z-axis drive mechanism and the X-axis drive mechanism, in the Y-direction relative to the supporting frame. The second pair of linear motors may be larger and of a higher power than the first pair of linear motors, as they are required to move a greater mass than the first pair of linear motors. Linear motors of this type are available from Aerotech, Inc., 101 Zeta Drive, Pittsburgh, Pa. 15238. USA. The second pair of linear motors 244 on the first frame 120 forms part of the Y-axis drive mechanism.

It should be clear that although this arrangement has been described in relation to a system for inspecting semiconductor wafers in a clean room environment, it can also be used in x-ray inspection systems that do not need to operate in a clean room environment and so do not include the air movers and air filters described.

Sample Position Measurement

As explained, one of the requirements for producing good quality tomosynthesis models is very accurate knowledge of the relative position of the x-ray source, sample and detector. In particular, it is necessary to know accurately the change in relative positions from one imaging position to the next so that the images can be properly combined.

To provide high magnification images, the distance between the sample and the x-ray source is much smaller than the distance between the detector and the x-ray source. This means that small changes in position of the sample lead to large changes in the image recorded by the detector. This in turn means that the position of the sample needs to be known to a much higher accuracy than the position of the detector.

Figure 8:
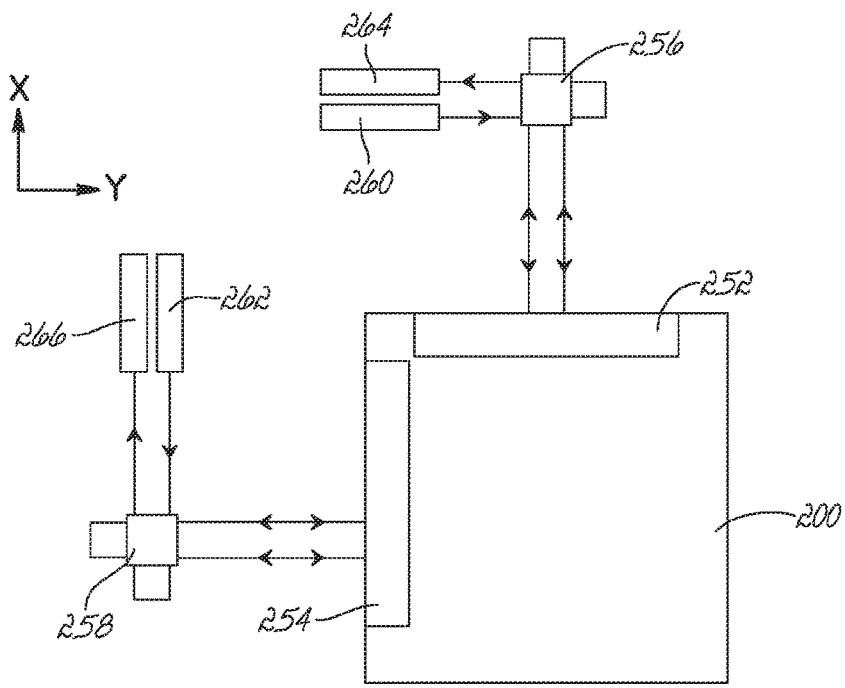
FIG. 8 is a schematic illustration of a sample support position detection system.

A non-contact position measuring device may be used to accurately determine the position of the sample support. In one embodiment of the invention, an interferometer based system is used to determine the changes in position of the sample support from one imaging position to the next. FIG. 8 is a schematic illustration of the interferometer based detection arrangement. Two interferometers are provided. A first interferometer 256 is used to determine changes in the position of the sample support 200 in the X-direction and a second interferometer 258 is used to determine changes in the position of the sample support in the Y-direction. The assemblies for the X- and Y-directions are identical. Each assembly comprises a laser light source 260, 262 that provides a laser beam to the associated interferometer 256, 258. The interferometer directs a portion of the laser beam to a mirror 252, 254 mounted to the sample support 200. Light reflected from the mirror is directed back to the interferometer and then to a detector 264, 266. Changes in the interference between light that has travelled to the sample support and light that has not travelled to the sample support, as the sample support is moved, is detected at the detector to provide a very accurate measure of the change in position of the sample support in the sensed (i.e. x or y) direction. Suitable interferometer systems, including the laser light sources and mirrors, are available from Renishaw plc, New Mills, Wotton-under-Edge, Gloucestershire, GL12 8JR, United Kingdom. Other possible non-contact position measuring devices include optical linear encoders, magnetic encoders, capacitive sensors and sonar distance measuring devices.

The output from the detectors is an accurate measure of the change in position of the sample support in the X- and Y-directions as the sample support moves between imaging positions. These measurements are provided to an image processor, as will be described, and used in a tomosynthesis calculation. The measurements from the detectors may also be used to calibrate the X and Y positioning assemblies.

FIG. 8 illustrates an arrangement in which a separate laser light source is provided for each interferometer. However, it should be clear that a single laser light source and a beam splitter could be used. Furthermore, it is possible to use an identical arrangement to determine changes in position of the sample support in the Z-direction, although the position of the sample support in the Z-direction typically does not need to be determined with such a high degree of accuracy.

Figure 9:
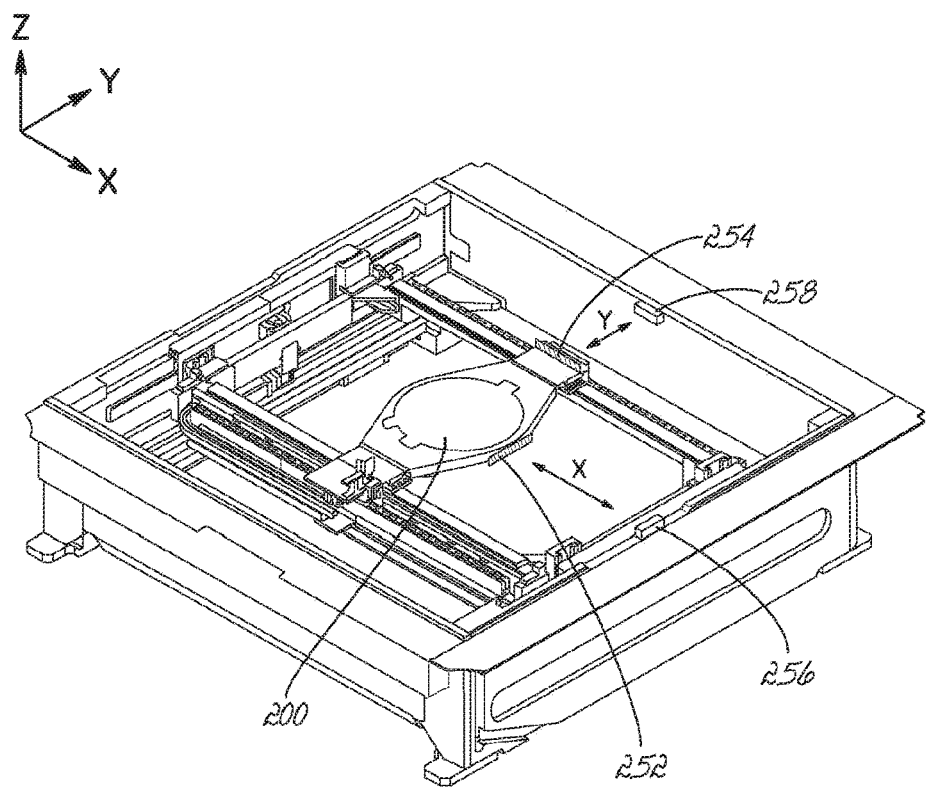
FIG. 9 is a perspective view illustrating the location of the position detection system of FIG. 8 in the sample positioning assembly of FIG. 7.

FIG. 9 illustrates how the arrangement as illustrated in FIG. 8 is integrated into the sample positioning assembly shown in FIG. 7. The first mirror 252 is fixed to the sample support 200 facing in the X-direction and the second mirror 254 is fixed to the sample support facing in the Y-direction. The interferometers 256, 258 are fixed to the supporting frame 120. The mirrors 252, 254 have sufficient height and width that light from the interferometers 256, 258 is incident on the mirrors in all possible imaging positions. In this example, the usable area of each mirror is 320 mm wide and 20 mm high. The mirrors are typically provided as part of the interferometer system as described above. However, suitable mirrors are also available as standalone items from optics manufacturers, such as Gooch and Housego PLC, Dowlish Ford, Ilminster, TA19 0PF, UK.

It should be clear that although this arrangement has been described in relation to a system for inspecting semiconductor wafers in a clean room environment, it can also be used in x-ray inspection systems that do not need to operate in a clean room environment and so do not include the air movers and air filters described. It may also be used in conjunction with a different arrangement for positioning the sample and the detector.

Proximity Measurement

As described, for high magnification images it is necessary to bring the sample very close to the x-ray source. It is therefore necessary to control the position of the sample in the Z-direction reliably. It is also necessary to know the position of the sample in the Z-direction for image processing and data interpretation purposes.

While the position of the sample support 200 in the Z-axis can be determined from the Z-axis positioning mechanism or from a linear encoder mounted to the Z-axis positioning mechanism, there is the problem that different samples have different thickness and so the actual distance between the x-ray source and a top surface of the sample cannot be determined accurately from the position of the sample support 200. Accordingly, in one aspect of the invention, a proximity sensor is used to provide a direct measurement of the distance between a top surface of the sample and the x-ray source.

Providing a direct measurement of the distance between the x-ray source and the top surface of a sample is beneficial for several reasons, particularly in a high magnification system in which the top surface of the sample, which typically comprises the regions of interest, is brought very close to the x-ray source. First, the distance measurement can be used to calibrate the Z-axis positioning mechanism, so that accurate positioning and subsequent image processing can be achieved. Second, the distance measurement can be used directly in a magnification calculation to provide an accurate measure of magnification. Third, the distance measurement or multiple distance measurements can be used to prevent any collision between the top surface of the sample and the x-ray source, which would likely be very damaging to both.

Figure 10:
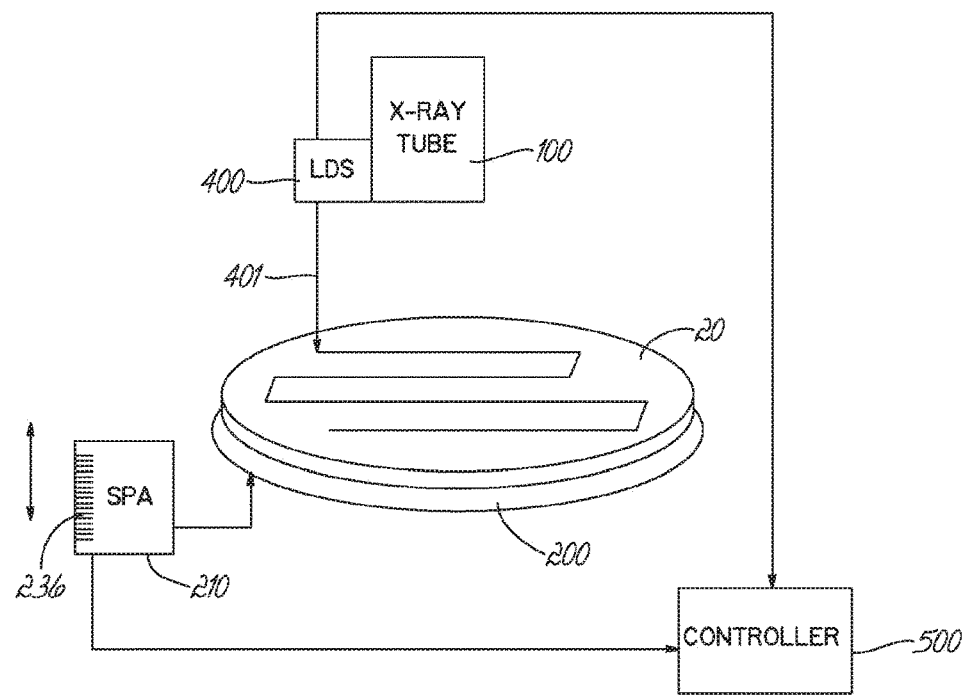
FIG. 10 is a schematic illustration of a sample proximity sensor assembly.

FIG. 10 is a schematic illustration of a proximity sensing arrangement in accordance with an aspect of the invention. A semiconductor wafer 20 is illustrated on a sample support 200, beneath a sealed x-ray tube 100. A laser distance sensor 400 is fixed to the x-ray tube 100. A suitable laser distance sensor is available from Keyence Corporation, 1-3-14, Higashi-Nakajima, Higashi-Yodogawa-ku, Osaka, 533-8555, Japan. As an alternative, a confocal detector may be used. A laser beam from the distance sensor is indicated by arrow 401. The sample positioning assembly 210 is illustrated schematically and includes a linear encoder 236 for determining a Z-axis position of the sample support 200. Both the sample positioning assembly and the distance sensor are connected to a controller 500.

Figure 11:
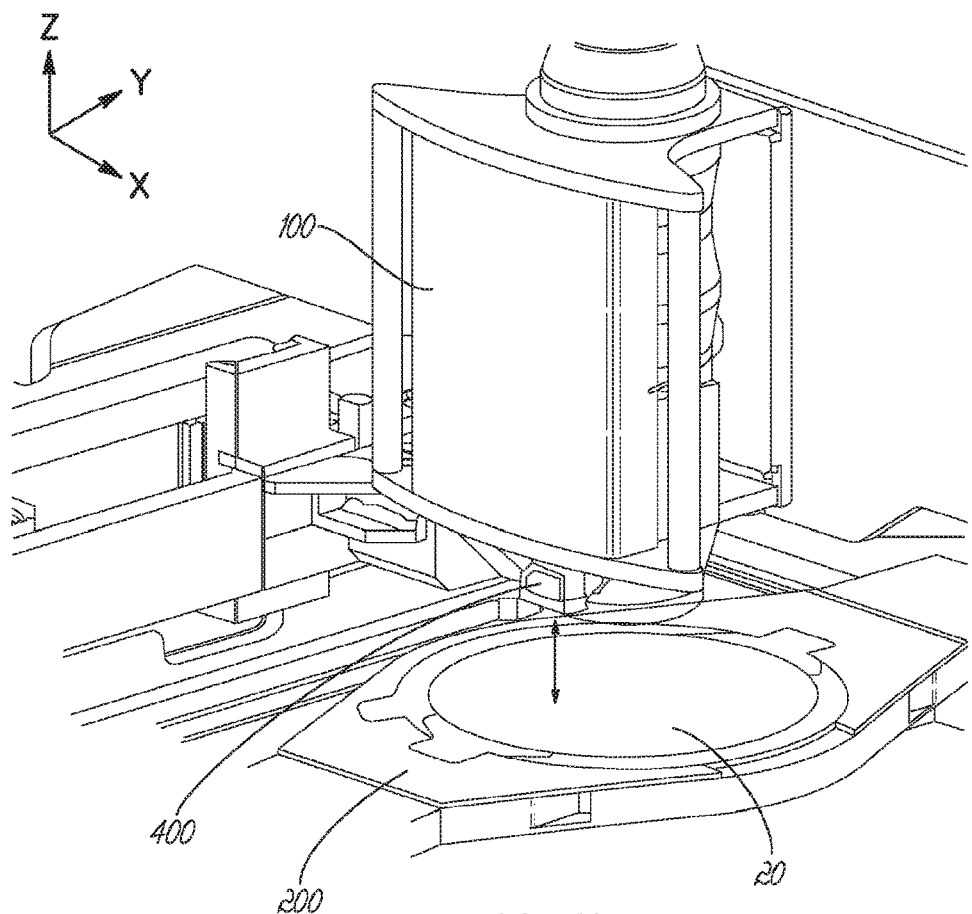
FIG. 11 is a perspective view illustrating the position of the proximity sensor in an x-ray inspection system of the type shown in FIG. 2.

FIG. 11 illustrates the mounting of the laser distance sensor 400 to the x-ray tube 100 in a system of the type shown in FIGS. 2, 3 and 4.

Figure 12:
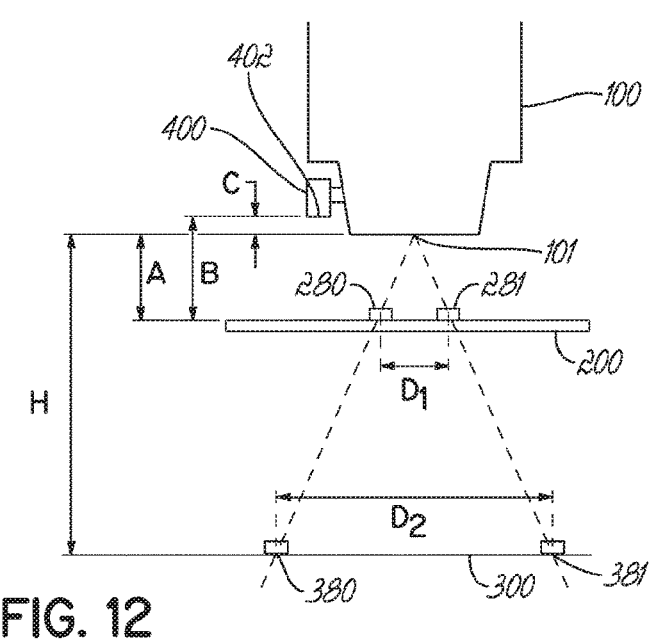
FIG. 12 is a schematic diagram illustrating the distances used in a proximity calculation and in a magnification calculation.

The laser distance sensor 400 provides a direct measurement to the top surface of the sample, in this example a semiconductor wafer. The laser distance sensor 400 measures the distance to the sample from its output end, herein referred to as the read head facing the top surface of the sample. The x-ray tube 100 produces x-rays from an output spot on the transmission target. The transmission target forms the output window 101 of the x-ray tube, so that the output spot lies in the plane of the output window 101 of the x-ray tube 100. The read head of the laser distance sensor 400 may not be mounted at exactly the same height as the output spot of the x-ray tube 100. In other words, the read head of the laser distance sensor may not be coplanar with the output window of the x-ray tube. But the difference in height between the output window and the output end of the laser distance sensor, known as the offset, can be calculated during system set-up by imaging a feature of known size, or two features of known spacing, on the sample support, in different positions as explained below FIG. 12 is a schematic illustration of the arrangement shown in FIG. 11, showing how the offset between the read head 402 of the laser distance sensor 400 and the output window 101 of the x-ray tube can be calculated by imaging a pair of features 280, 281 of a known spacing from one another on a gauge plate on the sample support 200.

The known distance between the features 280 and 281 on the gauge plate is $D_1$. The distance between the images 380, 381 of the two features 280, 281 on the detector 300 is $D_2$. $D_2$ can be determined from the output of the detector using standard image processing techniques.

It is well known in this field that the ratio $D_1/D_2$ is equal to the ratio A/H. The distance H between the output window of the x-ray source and the imaging surface of the detector 300 is known from the system specifications. So A can be calculated using the formula:

$$A = H \times (D_1/D_2).$$

The distance B between the read head of the laser distance sensor and the sample support is directly measured by the laser distance sensor 400. Consequently, the offset C between the read head of the laser distance sensor 400 and the output window of the x-ray tube is determined by subtraction:

$$C = B - A.$$

Since, $A = H \times (D_1/D_2)$, $C = B - (H \times (D_1/D_2))$.

Therefore, the difference in height, or offset C, between the output window and the read head of the laser distance sensor can be calculated from the formula $C = B - H \times (D_1/D_2)$ during system set-up by imaging a feature of known size.

Subsequent measurements of the distance to the sample from the read head of the laser distance sensor can be adjusted by this offset C to get the distance from the output window to the sample, which is used in magnification calculations as explained below.

The laser distance sensor can then be used to calibrate a height sensor within the sample positioning assembly. In this example, the height sensor is the linear encoder 236, which is used in the Z-axis sample positioning mechanism, as shown in FIG. 10. This is particularly beneficial if, during inspection, the sample is positioned so that it is obscured from the laser distance sensor by the x-ray tube so that the laser distance sensor measurements cannot be used directly. When the sample is in a position that it is not obscured by the x-ray tube, referred to here as the starting position, the controller 500 receives distance measurements from the laser distance sensor 400 and at the same time receives an output from the linear encoder 236. The absolute distance between the top plane of the sample and the output window of the x-ray tube can be established using the laser distance sensor 400. This is done by taking the absolute measurement reading from the laser distance sensor 400 and subtracting the offset C, calculated as described. This distance between the top plane of the sample and the output window of the x-ray tube is then used as the calibration for the linear encoder, which measures changes in distance from the starting position. This calibration process can be carried out periodically.

In addition, the laser distance sensor measurements can be used to determine image magnification, which is used during image processing. Image magnification (IM) is the ratio of the size of the object as it appears in the image on the detector 300 to the actual size of an object. With reference to FIG. 12, it is known in this field that the magnification ratio is equal to H/A. A is determined from the measured distance B minus the calculated offset C. H is a known value. So image magnification is given by the formula:

$$IM = H/A = H/(B-C).$$

For example, if the distance H is 350 mm, the measured distance B is 12 mm and the offset value C has been calculated as 2 mm, then the image magnification will be:

$$IM = H/(B-C) = 350/(12-2) = 35.$$

This means that a distance between features that appears as a 35 mm distance on the detector is an image of a real distance of 1 mm.

This ability to accurately determine magnification has two benefits. Firstly, the size of the features within the sample can be established very accurately, allowing good quantitative assessment of geometric feature sizes such as wafer bump diameter or void area. Secondly, during tomosynthesis, the angle and location of individual projections is well known, so the computed three-dimensional model can be made accurate. An image magnification calculation using measurement from the laser distance sensor is typically carried out as a calibration calculation before a set of images of a particular region or regions of interest are captured.

It should be clear that although this arrangement has been described in relation to a system for inspecting semiconductor wafers in a clean room environment, it can also be used in x-ray inspection systems that do not need to operate in a clean room environment and so do not include the air movers and air filters described.

Collision Prevention

The proximity sensor, or laser distance sensor, 400 illustrated in FIGS. 10, 11 and 12 can also be used to prevent any collision between the x-ray source and the sample. A collision between the x-ray source and the sample is likely to irreparably damage the sample and also cause significant damage to the x-ray tube. Because samples, in this example semiconductor wafers, can have different thicknesses, simply relying on an output from the linear encoder 236 which only provides information about the position of the sample support, may not be effective at preventing collision when trying to obtain very high magnification images, which require that the sample be placed very close to the x-ray tube, making the distance A in FIG. 12 very small.

In order to prevent collision, prior to inspection of a semiconductor wafer at high magnification, the wafer is safely raster scanned by the laser distance sensor at a low magnification height, which is known to be safe for all possible wafers, to establish the distance of the top-most feature on the wafer 20 from the end of the x-ray tube 100. The raster scan is achieved by operating the sample positioning assembly to move the sample support in the XY plane. This illustrated in FIG. 10. The location on the linear encoder scale is recorded for the low magnification height as a baseline value. The shortest distance measured by the laser height sensor, corresponding to top-most feature on the wafer 20, is recorded. The controller 500 then creates a virtual reference plane based on the baseline encoder scale reading at the measured shortest distance which dictates how close the wafer can safely be brought to the surface of the x-ray tube. The virtual plane may be located at a predetermined clearance above the top-most feature on the wafer. For example, if the shortest distance to the top of the sample measured by the laser distance sensor at the low magnification height is 12 mm and the known offset between the output end of the laser distance sensor 400 and the output window of the x-ray tube, C, is 2 mm, then the shortest distance between the output window of the x-ray tube and the top of the sample during the raster scan is 10 mm. If it is desired that in operation the top surface of the sample should be no closer than 1 mm from the output window of the x-ray tube in order to prevent any possibility of a collision, then the sample support can be moved no closer than 9 mm from the low magnification height recorded as a baseline on the linear encoder. This 9 mm maximum travel can be controlled using the linear encoder readings. The linear encoder scale can be used during inspection of the wafer to ensure that no collision can occur.

Figure 13:
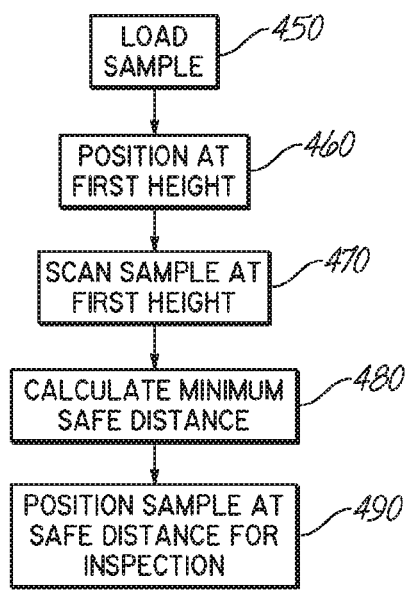
FIG. 13 is a flow diagram illustrating a collision prevention operation.

FIG. 13 is a flow diagram illustrating the control process used to prevent collision between the x-ray tube and the wafer. In step 450 a semiconductor wafer is loaded into the system. In step 460, the wafer is positioned below the laser distance sensor at a known safe height, i.e. at a height at which even the very thickest sample would be well clear of the x-ray tube. In step 470 the laser distance sensor is then activated and the sample support moved in a raster scan pattern in the XY plane by the sample positioning assembly. The distance to the closest feature on the wafer is recorded. In step 480 the maximum permitted upward travel of the sample support is calculated corresponding to a minimum safe distance between the sample support and the x-ray tube or a maximum safe height for the sample support. In step 490 inspection of the wafer is performed at high magnification but with the sample support at a position lower than or equal to the maximum safe height for the sample support.

This process can be performed quickly and automatically for every new sample that is loaded into the machine. Again, it should be clear that this system and method is applicable not only to semiconductor wafers but to any type of sample that is required to be imaged at high magnification.

Detector Positioning

As described, the x-ray detector is positioned below the sample support to capture x-rays that have passed through the sample. The detector is a flat panel detector that includes a two dimensional pixel array of silicon photodiodes, as previously described.

In order to record different projections through a sample, the detector must be moved accurately to different imaging positions. The projections are then combined using a tomosynthesis algorithm to generate a three-dimensional model of the sample or of a region of the sample. As described, it is desirable for the plurality of different projections to be recorded as quickly as possible. And for high magnification images, in which the sample support is positioned very close to the x-ray source, the x-ray detector must move much greater distances between imaging positions than the sample support, and so it is necessary for the detector to be moved at a relatively higher speed than the sample support.

In order that the detector can be moved accurately but at a high speed it is advantageous that the detector be moved within the XY plane, on rigid axes. The alternative of moving the detector on a pivotable, arcuate track, which has been used in prior systems, does not allow for such accurate movement at high speed because the mechanism is less rigid. This alternative system would also suffer from excessive vibration when starting and stopping at high speed. Movement of both the detector and sample within parallel XY planes, without any Z-axis movement, also has the advantage that the image magnification remains the same for all imaging positions, as the magnification is determined by the formula IM=A/H as previously discussed.

However, movement of a detector having the detector face that lies in the XY plane solely within that XY plane suffers from the disadvantage that the detector is not always facing the x-ray source. At extreme oblique angles between the face of the detector and the point of emission of the x-rays from the x-ray source blurring of the image can occur. In one aspect of the invention, a tilting mechanism is provided for the detector, in addition to a mechanism for moving the detector in an XY plane, which allows the detector to be oriented so that it faces the x-ray source in all imaging positions.

Figure 14:
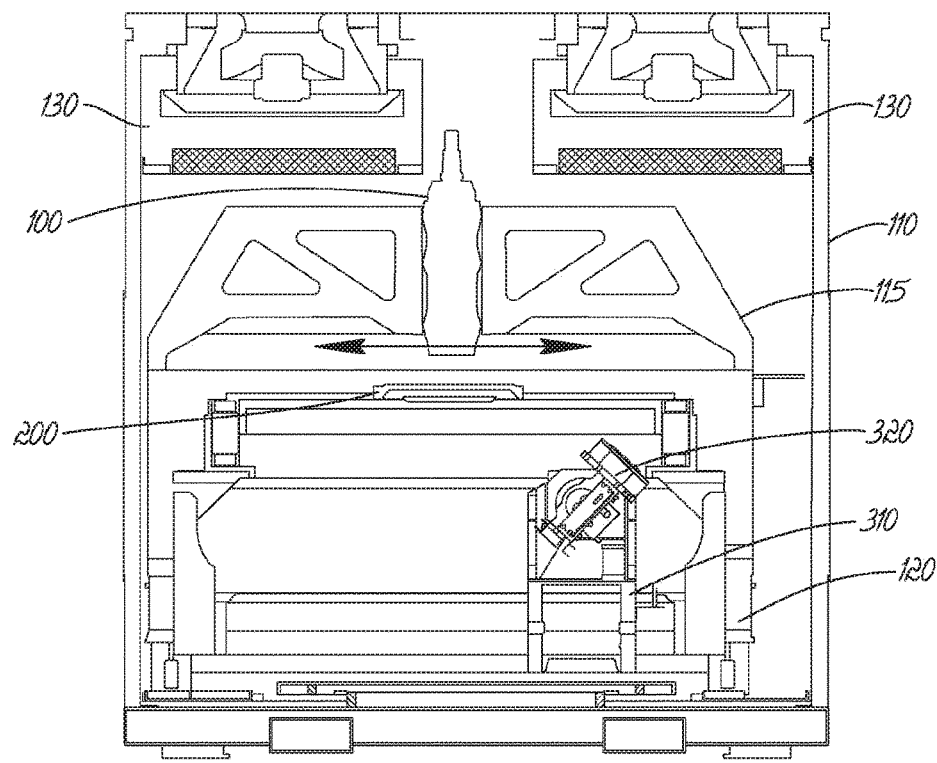
FIG. 14 is a schematic cross-section illustration of an x-ray inspection system in accordance with the invention showing a tilting mechanism for the x-ray detector.

FIG. 14 is a schematic cross-section illustration of an x-ray inspection system in accordance with the invention, as illustrated in FIG. 2 but showing a tilting mechanism 320 for the x-ray detector. The detector positioning assembly 310 allows the detector 300 to move in a horizontal plane.

The remaining features of the system shown in FIG. 14 are as described with reference to FIG. 2. The cabinet and FFUs are configured for clean room operation. A sample positioning stage 210 is provided on the supporting frame above the detector positioning stage. The detailed components of the sample positioning stage are shown in, and described with reference to, FIGS. 6 and 7. The x-ray tube 100 is fixed to the bracket 115 and is positioned above the sample support 200 and the detector 300.

In order to provide for high speed movement in the XY plane, first and second linear motors are used to move the detector in the x direction and y direction respectively. As illustrated in FIG. 15, a first linear motor 312 is mounted between a frame 326 of the detector assembly and a horizontally extending beam 314. The beam 314 extends in the X-direction and is supported to move along the supporting frame 120. To provide for this movement, a pair of second linear motors 316 (only one of which is visible in FIG. 15), extending in the Y-direction, is mounted on the supporting frame 120 and drive the remote ends 315 of the beam 314. Activation of the first linear motor 312 moves the detector assembly along the beam 314 in the X-direction. Activation of the second linear motors 316 moves the beam 314 and the detector assembly in the Y-direction, which is perpendicular to beam 314.

This mechanism allows the detector to be moved within a horizontal plane quickly and accurately. The first and second linear motors may be identical and are larger that the linear motors used for the sample support positing assembly. Linear motors of this type are available from Aerotech, Inc., 101 Zeta Drive, Pittsburgh, Pa. 15238. USA.

FIG. 16 shows the tilting mechanism 320 in detail. Two further axes of movement for the detector are provided by this tilting mechanism 320 so that the planar imaging surface, or face 305, of detector 300 is always able to be faced directly at the x-ray source. The detector 300 is mounted to a first gimbal frame 322 so that it can be tilted about a first rotary axis 321. A first motor 324 is configured to rotate the detector about the first rotary axis. One example of a suitable motor is the APR150DR-135 from Aerotech Inc., 101 Zeta Drive, Pittsburgh, Pa. 15238, USA.

The first gimbal frame 322 is rotatably mounted to a motor 328, which is mounted to second gimbal frame 326, to rotate about a second rotary axis 327. The second motor 328 is configured to rotate the first gimbal frame 322 about the second rotary axis 327. The second gimbal frame 326 is mounted to the mover of linear motor 312 and the stator of linear motor 312 is mounted to the beam 314, as described with reference to FIG. 15, so that the detector and tilting mechanism can be move along the beam 314. The first and second motors comprise direct read encoders on an output side to allow for a very accurate determination of the orientation of the detector.

The tilting mechanism is arranged so that the first and second rotary axes 321, 327 are coplanar with the active area, or face 305, of the detector. This means, as shown in FIG. 16, that both first rotary axis 321 and second rotary axis 327 run across, or align with, the face 305 of the detector 300. This simplifies the image processing calculations required. It also removes the need for any compensatory Z-axis movement of the sample support or detector to address changes in image magnification. This is because the centre of the face of the detector remains at the same Z-axis distance from the x-ray source in all positions and so the image magnification remains constant regardless of the position of the tilting mechanism.

The first and second rotary motors are connected to and controlled by a controller (not shown in FIG. 16) that is also connected to the linear motors for the XY movement of the detector. The controller is configured to ensure that in each imaging position in which the detector is stopped to record an x-ray image, the active area 305 of the detector is facing the x-ray source. Preferably, the controller will orient the active area, or face 305, of the detector so that it is perpendicular to a line drawn from the centre of the face of the detector to the point at which the x-rays are emitted from the x-ray source.

By constantly facing the active area 305 of the detector towards the x-ray source, oblique angles between the face of the detector and the point of emission of the x-rays from the x-ray source, which can cause blurring of the image, are avoided. This improves the quality of the image.

It should be clear that although this arrangement has been described in relation to a system for inspecting semiconductor wafers in a clean room environment, it can also be used in x-ray inspection systems that do not need to operate in a clean room environment and so do not include the air movers and air filters described. It is also possible to use this detector positioning assembly with a different arrangement for the sample support position assembly and without the position detection systems so far described.

Wafer Chuck

Figure 17:
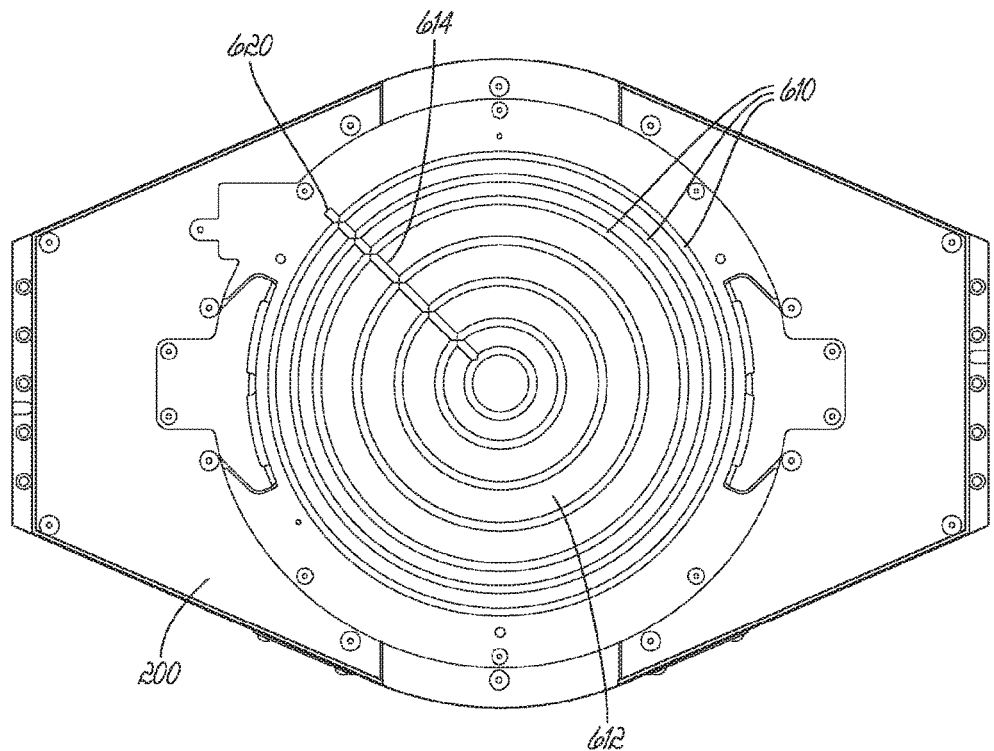
FIG. 17 is a perspective view of a sample support for a semiconductor wafer.

The sample support 200 for the semiconductor wafers 20 holds each semiconductor wafer in position by applying suction to a rear surface of the wafer. This is a well known wafer handling technique that avoids damage to the wafer. FIG. 17 is a plan view of the sample support and shows a plurality of concentric depressions or grooves 610 formed in a planar upper support surface 612 of the sample support. The grooves 610 are connected to a vacuum port 620 by a radial channel 614. When a wafer is placed onto the support surface 612 a vacuum is applied to the port 620. This holds the wafer firmly against the support surface 612. The "imaging area" of the sample support is the portion of the sample support that may appear in an x-ray image of a portion of the semiconductor wafer.

In an x-ray inspection system as described, x-rays from the x-ray tube 100 not only pass through the semiconductor wafer but must also pass through the sample support 200 before reaching the detector 300. The sample support must therefore be made from a material that does not attenuate the x-rays to too great an extent and does not have a crystalline structure that would diffract x-rays. Suitable materials include polyether ether ketone (PEEK), beryllium, and acetal.

Figure 19:
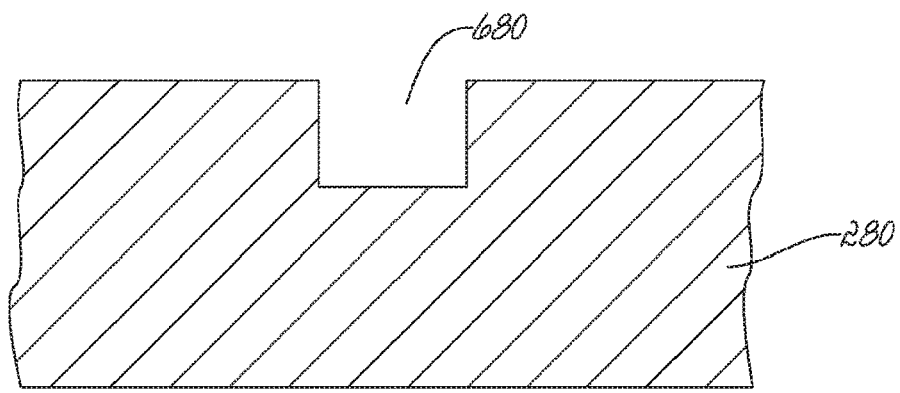
FIG. 19 is a schematic cross-section of a portion of a typical wafer chuck in accordance with the prior art.

However, even these materials will attenuate the x-rays to some extent. The amount of attenuation depends on the thickness of the sample support that the x-ray must pass through. The grooves 610 result in a local thinning of the sample support and so the pattern of thickness changes caused by the grooves will appear in the resulting x-ray images. The groves of a conventional wafer chuck are rectangular in cross-section with parallel sidewalls and a flat bottom, as shown in FIG. 19. FIG. 19 shows a wafer chuck 280 with a rectangular cross-section groove 680. If the x-ray image spans a groove, x-rays that pass a groove on the wafer chuck will be less attenuated than those that pass through the remainder of the wafer chuck. The rectangular cross-section means that, given the vertical sidewalls of the grooves, the change in wafer chuck thickness is very abrupt. This can cause very sudden changes in contrast in the x-ray image that would obscure or confuse the image, particularly of weakly contrasting features of a wafer. This in turn would make automated analysis of the images slow or even impossible in some cases.

To minimise this problem, rather than providing grooves having rectangular cross-sections, the grooves or depressions used in the present invention for providing suction to the rear of a wafer are configured to provide only small and gradual changes in wafer chuck thickness to cause less patterning in the x-ray image that would obscure or confuse the image. Thus, the thickness of the wafer chuck is continuously varied rather than having sudden changes in thickness, and the grooves are made comparatively wide and shallow.

Figure 18:
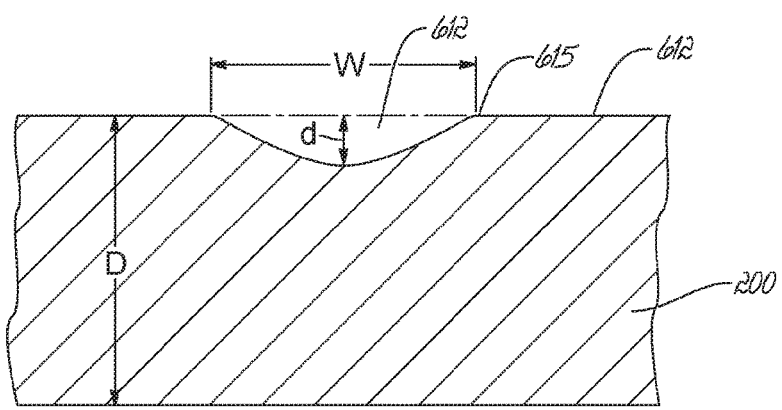
FIG. 18 is a schematic cross-section of a portion of the sample support of FIG. 17.

FIG. 18 is a schematic cross-section of one of the grooves 610 of FIG. 17 in accordance with the invention. In this example the groove has a width W of around 4.88 mm and a maximum depth below the support surface of 0.2 mm. The sidewall of the groove extends in a continuous curve from a first side to a second side of the groove. The curve is substantially circular and has a maximum radius of curvature of around 16 mm. It can be seen that the radius of curvature is substantially two orders of magnitude greater than the maximum depth of the groove. This ensures that the rate of change of thickness of the wafer check is small. The maximum thickness of the sample support in the imaging area D is 5 mm.

The size and shape of the grooves must satisfy two competing requirements. The grooves must be large enough to provide a sufficient suction force on the back of the wafer. But they must also not obscure or confuse images of features of interest in or on a semiconductor wafer.

In this example, the depth of the groove increases to 0.2 mm over a radial distance of 2.44 mm, which corresponds to about a 4% change in the thickness of the wafer since 0.2 mm/5 mm=0.04. The average rate of change of thickness of the wafer across the groove is 0.2/2.44=0.8 mm change in thickness per mm of travel parallel to the planar support surface. The maximum rate of change of thickness of the wafer is at the edge of the depression and is approximately 0.165 mm per mm of travel parallel to the planar support surface.

The width of the groove W is two orders of magnitude greater than the typical features of interest within a semiconductor wafer. As the groove varies continuously across its width rather than having sharp edges, this means that at a magnification appropriate for inspection, only around 1% of the total thickness variation across the groove is seen as variation in the image background of a feature of interest.

When examining a 100 μm diameter solder bump on a silicon wafer, analysis software may use four points outside of the bump area to determine a baseline for adjusting image contrast. In the worst case, these points will be 200 μm apart from each other. If the solder bumps overlie the edge of a groove, where the rate of change of thickness of the chuck is at its highest, the effective depth of the sample support will vary by about 0.66% across the imaged area. This is calculated as the maximum rate of change of depth×diameter of region of interest/maximum thickness of chuck 0.165×0.02/5≈0.066%. This does not give rise to a significant change in image contrast across the image compared to the contrast provided between the solder bump and its surrounding area and any defects in the solder bump.

It is desirable not to have any sharp edges in the grooves or depressions. In other words, the rate of change in the change of thickness of the sample support should be low. This is to ensure that there are no sharp edges that might be enhanced by edge detection algorithms in the image processing software used. By providing depressions that extend in a continuous curve from one side to another, sharp edges are avoided within the depression themselves. The edges of the depressions should also ideally be smooth. As can be seen in FIG. 18 the edges 615 of the groove 610 are rounded to remove any sharp transitions. The radius of curvature of the transition region between the sidewall of the groove and the planar support surface 612 has a minimum radius of curvature of around 2 mm.

It should be clear that this is just one example of a wafer support in accordance with the invention and that different geometries for the groves can be used that provide a low maximum rate of change of thickness of the support across the imaging area. Clearly the required dimensions of the grooves depend on the size and nature of the regions to be imaged and on the density of the material (which is closely related to how strongly x-rays are attenuated) of the sample support compared to the density of the samples being imaged.

System Operation

The various aspects of the x-ray inspection system so far described can be controlled to operate automatically and synchronously with each other. In particular the positioning of the sample support and of the detector must be co-ordinated and informed by measurements from the position detection arrangements. The air movers, x-ray tube and wafer handling equipment must also be co-ordinated with the positioning assemblies.

Figure 20:
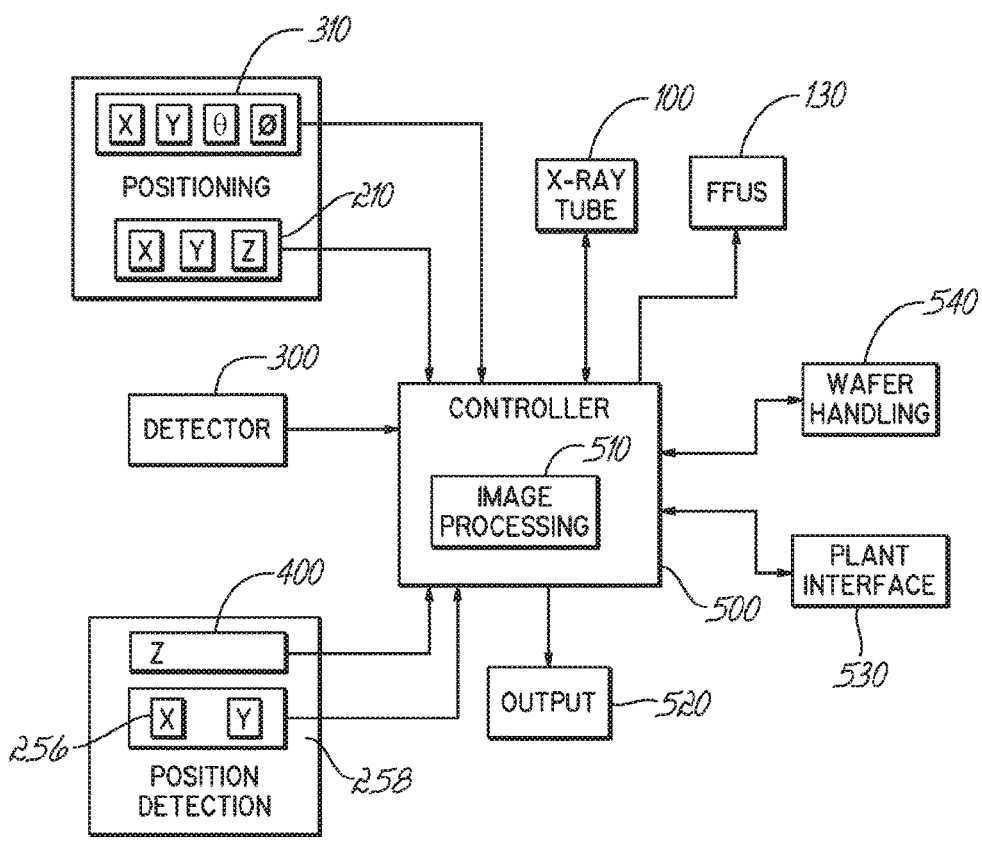
FIG. 20 is a schematic diagram showing the control elements of the x-ray inspection system.

FIG. 20 is a schematic diagram illustrating the use of a central controller 500, to co-ordinate the operation of each of the controllable components of the system and to receive and process the data required to provide a tomosynthetic model.

A central controller 500, including an image processor 510 is connected to each of the controllable components of the system, as well as to an output 520 and a fabrication plant interface 530.

The controller 500 controls operation of the x-ray tube 100 as well as the FFUs 130. It operates an automated wafer handling mechanism 540 that extends through the shutter to place a wafer onto the sample support 200 and also removes the wafer from the sample support 200 after the wafer has been inspected within the system. It positions the wafer through the sample support positioning assembly 210 and correspondingly controls the detector through the detector positioning assembly 310. It receives the output from the detector to build the three-dimensional model. It receives input from the laser distance sensor 400 to control the vertical position of the wafer relative to the x-ray source to avoid a collision. Input from the laser distance sensor 400 is also used in image magnification calculations. It also receives inputs from the interferometers which indicate the change in position of the sample support 200 as it moves to different positions for images to be collected.

The controller coordinates the movement of the sample support and the detector in accordance with a pre-programmed sequence of operation as well as performing initial calibrations as previously described. The controller must both control the sample stage, which has three axes of movement, and the detector, which has four axes of movement, two of them being rotational.

Figure 21:
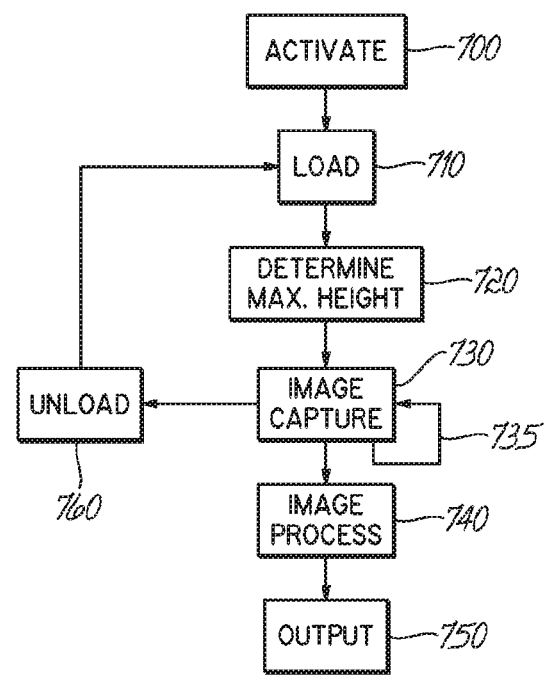
FIG. 21 is flow diagram illustrating the operation of the x-ray inspection system in a continuous manner.

FIG. 21 is a flow diagram illustrating an exemplary cycle of operation for an x-ray inspection system of the type illustrated in FIG. 20. The system is activated in step 700. In this step, the controller is switched on and the FFUs are subsequently switched on to establish a laminar air flow. The FFUs then run continuously during operation of the system. In step 710, the wafer handling assembly 540 is operated to load a semiconductor wafer into the system onto the sample support. The wafer handling assembly in this embodiment comprises conventional wafer handling equipment used in semiconductor fabrication plants, in this example the Brooks JET™ Atmospheric Transport System described earlier. The wafer is secured on the sample support using suction, as described. In step 720 the maximum height for the sample support is calculated using the process described with reference to FIG. 10-12. In step 730 the x-ray tube 100 is activated and projections of a plurality of different regions of interest on the wafer are recorded by the detector 300. In this process the sample support 200 and detector 300 are moved to a plurality of predetermined imaging positions. This process may be repeated for different regions of interest on the wafer as indicated by arrow 735. In step 740 the projections of a particular region of interest are processed using a tomosynthesis algorithm to generate a three-dimensional model. The image processor 510 uses the recorded images from the detector as well as associated information about the position of the sample, sample support and detector for each image. This model is output to a display and/or memory in step 750, together with any other collected data relating to the image capture process. After all of the required images for a particular wafer have been captured by the detector 300, the wafer is unloaded from the system in step 760 using the wafer handling assembly 540, and new wafer can then be loaded in step 710. The unloading and loading of wafers can be carried out simultaneously with the image processing operations.

The system can be integrated into a semiconductor fabrication plant. Automatic loading and unloading of semiconductor wafers to and from the sample support, at any desired point in the wafer processing operation and/or after wafer processing has been completed, can be achieved using standard wafer handling equipment. Control software for the positioning assemblies, detector and x-ray tube can be integrated with the fabrication plant control system for the controller 500.

The invention claimed is:

1. An x-ray inspection system, comprising:
a cabinet, the cabinet containing an x-ray source, a sample support for supporting a sample to be inspected, and an x-ray detector;
an air mover configured to force air into the cabinet through an air inlet in the cabinet above the sample support, wherein the air mover and the cabinet are configured to force air through the cabinet from the air inlet past the sample support to an air outlet in the cabinet below the sample support; and a sample support positioning assembly for positioning the sample support relative to the x-ray source and the x-ray detector, wherein the sample support comprises an upper surface extending in a horizontal plane and wherein the sample support positioning assembly comprises a vertical positioning mechanism for moving the sample support in a vertical direction, orthogonal to the horizontal plane, and a first horizontal positioning mechanism for moving both the sample support and the vertical positioning mechanism in a first horizontal direction, wherein the x-ray source is located above the sample support, and wherein the air inlet comprises a labyrinthine air flow path.

2. The x-ray inspection system of claim 1, wherein the horizontal plane of the sample support is a first horizontal plane, further comprising a detector positioning assembly for positioning the x-ray detector relative to the x-ray source, wherein the detector positioning assembly comprises a horizontal detector positioning mechanism for moving the x-ray detector in at least two non-parallel directions within a second horizontal plane, and a detector tilting mechanism configured to allow the x-ray detector to be tilted from the second horizontal plane about at least two non-parallel axes.

3. The x-ray inspection system of claim 1, further comprising a proximity sensor fixed to the x-ray source and configured to provide a measurement of distance between the x-ray source and a surface of the sample on the sample support and a controller connected to the proximity sensor.

4. The x-ray inspection system of claim 1, further comprising:

a sample support position detection assembly comprising a non-contact position measuring device positioned adjacent to the sample support and configured to detect a position or a change in position of the sample support; and an image processor connected to the x-ray detector and to the sample support position detection assembly.

5. The x-ray inspection system of claim 1, wherein the air outlet includes a labyrinthine air flow path.

6. The x-ray inspection system of claim 1, wherein the air mover includes an x-ray shield arranged to prevent the escape of x-rays from the cabinet.

7. An x-ray inspection system, comprising:

a cabinet;

an x-ray source disposed in the cabinet;

a sample support disposed in the cabinet and configured to support a sample to be inspected, wherein the sample support comprises a support surface extending in a first horizontal plane;

an x-ray detector disposed in the cabinet and configured to detect x-rays that have passed through the sample such that an image of the sample is recorded;

a sample support positioning assembly disposed in the cabinet and configured to position the sample support relative to the x-ray source or the x-ray detector; wherein the support sample positioning assembly comprises a vertical positioning mechanism for moving the sample support in a vertical direction, orthogonal to the first horizontal plane, and a first horizontal positioning mechanism for moving both the sample support and the vertical positioning mechanism in a first horizontal direction;

a detector positioning assembly disposed in the cabinet and configured to position the x-ray detector relative to the x-ray source, wherein the detector positioning assembly comprises a horizontal detector positioning mechanism for moving the x-ray detector in at least two non-parallel directions within a second horizontal plane, and a detector tilting mechanism configured to allow the x-ray detector to be tilted from the second horizontal plane about at least two non-parallel axes; and an air mover configured to force air into the cabinet through an air inlet in the cabinet above the sample support, wherein the air mover and the cabinet are configured to force air through the cabinet from the air inlet past the sample support to an air outlet in the cabinet below the sample support, wherein the x-ray source is located above the sample support, and wherein the air inlet comprises a labyrinthine air flow path.

8. The x-ray inspection system of claim 7, further comprising a proximity sensor fixed to the x-ray source and configured to provide a measurement of distance between the x-ray source and a surface of the sample on the sample support and a controller connected to the proximity sensor.

9. The x-ray inspection system of claim 7, further comprising:

a sample support position detection assembly comprising a non-contact position measuring device positioned adjacent to the sample support and configured to detect a position or a change in position of the sample support; and an image processor connected to the x-ray detector and to the sample support position detection assembly.

10. The x-ray inspection system of claim 7, wherein the air outlet includes a labyrinthine air flow path.

11. An x-ray inspection system, comprising:

a cabinet;

an x-ray source disposed in the cabinet;

a sample support disposed in the cabinet and configured to support a sample to be inspected, wherein the sample support comprises a support surface extending in a first horizontal plane;

an x-ray detector disposed in the cabinet;

a sample support positioning assembly disposed in the cabinet and configured to position the sample support relative to the x-ray source or the x-ray detector; wherein the sample support positioning assembly comprises a vertical positioning mechanism for moving the sample support in a vertical direction, orthogonal to the first horizontal plane, and a first horizontal positioning mechanism for moving both the sample support and the vertical positioning mechanism in a first horizontal direction;

a sample support position detection assembly disposed in the cabinet and comprising a non-contact position measuring device positioned adjacent to the sample support and configured to detect a position or a change in position of the sample support; and an image processor connected to the x-ray detector and to the sample support position detection assembly;

a proximity sensor fixed to the x-ray source and configured to provide a measurement of distance between the x-ray source and a surface of the sample on the sample support and a controller connected to the proximity sensor; and an air mover configured to force air into the cabinet through an air inlet in the cabinet above the sample support, wherein the air mover and the cabinet are configured to force air through the cabinet from the air inlet past the sample support to an air outlet in the cabinet below the sample support,
wherein the air inlet comprises a labyrinthine air flow path.

12. The x-ray inspection system of claim 11, further comprising a detector positioning assembly for positioning the x-ray detector relative to the x-ray source, wherein the detector positioning assembly comprises a horizontal detector positioning mechanism for moving the x-ray detector in at least two non-parallel directions within a second horizontal plane, and a detector tilting mechanism configured to allow the x-ray detector to be tilted from the second horizontal plane about at least two non-parallel axes.

13. An x-ray inspection system, comprising:
an x-ray source;
a sample support for supporting a sample to be inspected, wherein the sample support comprises a support surface extending in a first horizontal plane;
an x-ray detector;
a sample support positioning assembly that includes a first positioning mechanism for moving the sample support along a first axis towards and away from the x-ray source, and further comprising a proximity sensor fixed to the x-ray source and configured to provide a measurement of distance between the x-ray source and a surface of the sample on the sample support and a controller connected to the proximity sensor;
a sample support position detection assembly comprising a non-contact position measuring device positioned adjacent to the sample support and configured to detect a position or a change in position of the sample support; and
an image processor connected to the x-ray detector and to the sample support position detection assembly,
wherein the x-ray source is located above the sample support and the sample.

14. The x-ray inspection system of claim 13, further comprising:
a cabinet, the cabinet containing the x-ray source, the sample support, the sample support positioning assembly, the x-ray detector, and the sample support position detection assembly; and
an air mover configured to force air into the cabinet through an air inlet in the cabinet above the sample support, wherein the air mover and the cabinet are configured to force air through the cabinet from the air inlet past the sample support to an air outlet in the cabinet below the sample support.

15. The x-ray inspection system of claim 13, further comprising a detector positioning assembly for positioning the x-ray detector relative to the x-ray source, wherein the detector positioning assembly comprises a horizontal detector positioning mechanism for moving the x-ray detector in at least two non-parallel directions within a second horizontal plane, and a detector tilting mechanism configured to allow the x-ray detector to be tilted from the second horizontal plane about at least two non-parallel axes.

16. An x-ray inspection system, comprising:
a cabinet;
an x-ray source within the cabinet;
a wafer support within the cabinet configured to support a semiconductor wafer to be inspected;
a wafer support positioning assembly for positioning the wafer support relative to the x-ray source;
an x-ray detector within the cabinet;
a detector positioning assembly for positioning the x-ray detector relative to the x-ray source;
a wafer loading and unloading assembly configured to transport wafers from outside of the cabinet to the wafer support, and from the wafer support out of the cabinet;
a controller configured to control operation of the x-ray source, the wafer support positioning assembly, the detector positioning assembly and the wafer loading and unloading assembly; and
an image processor configured to process image data received from the x-ray detector, the image data relating to x-rays that have passed through the wafer,
wherein the x-ray source is located above the wafer support and the wafer.

17. The x-ray inspection system according to claim 16, further comprising at least one fan filter unit configured to force air through the cabinet from an air inlet above the wafer support to an air outlet below the wafer support.

18. The x-ray inspection system according to claim 16, further comprising a wafer support position detection assembly separate to the wafer support positioning assembly and configured to determine a position of the wafer support.

19. The x-ray inspection system according to claim 16, wherein the x-ray source is a sealed x-ray tube with a transmission target.

20. A method of imaging a semiconductor wafer using an x-ray inspection system, the method comprising:
activating an air mover configured to move air into the x-ray inspection system through an air inlet having a labyrinthine air flow path and through the x-ray inspection system;
loading the wafer into the x-ray inspection system;
positioning the wafer in an initial imaging position within the x-ray inspection system;
capturing an x-ray image of a region of interest of the wafer in the initial imaging position;
moving the wafer to a second imaging position;
capturing another x-ray image of a region of interest of the wafer in the second imaging position; and
unloading the wafer from the x-ray inspection system.

21. The method according to claim 20, further comprising performing a tomosynthesis calculation using the captured x-ray images.

22. The method according to claim 20, wherein the x-ray inspection system comprises an x-ray source and a sample support that is movable relative to the x-ray source, and wherein the step of positioning the wafer in the initial imaging position comprises scanning a surface of the wafer to determine how close the sample support can be brought to the x-ray source without a collision occurring between the x-ray source and the wafer.

23. The method according to claim 20, wherein the x-ray inspection system comprises an x-ray source and a sample support that is movable relative to the x-ray source, further comprising measuring a position of the sample support relative to the x-ray source using a non-contact position measuring device in each imaging position.

24. A method of imaging a sample that is supported on any sample support using an x-ray inspection system that has an x-ray tube located above the sample support, the method comprising:
using a distance sensor that detects the distance between the sample and the x-ray tube to prevent the sample from being positioned too close to the x-ray tube;
activating the x-ray tube and recording x-ray projections of a plurality of different regions of interest on the sample by a detector that is configured to detect x-rays that have passed through the sample; and utilizing input from the distance sensor in image magnification calculations.

* * * * *